United States Patent
Makriyannis et al.

(10) Patent No.: US 7,183,313 B2
(45) Date of Patent: Feb. 27, 2007

(54) KETO CANNABINOIDS WITH THERAPEUTIC INDICATIONS

(75) Inventors: Alexandros Makriyannis, Mystic, CT (US); Dai Lu, Storrs, CT (US); Xin-Zhong Lai, Storrs, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 10/647,544

(22) Filed: Aug. 25, 2003

(65) Prior Publication Data

US 2005/0074408 A1    Apr. 7, 2005

Related U.S. Application Data

(60) Provisional application No. 60/405,940, filed on Aug. 26, 2002, provisional application No. 60/405,608, filed on Aug. 23, 2002.

(51) Int. Cl.
*A61K 31/366*    (2006.01)
*C07D 311/80*    (2006.01)

(52) U.S. Cl. .................. 514/455; 549/280; 424/9.6
(58) Field of Classification Search ................ 514/455; 424/9.6; 549/280
See application file for complete search history.

(56) References Cited

U.S. PATENT DOCUMENTS

| | | | |
|---|---|---|---|
| 3,041,343 A | 6/1962 | Jucker et al. |
| 3,465,024 A | 9/1969 | Brownstein et al. |
| 3,573,327 A | 3/1971 | Miyano |
| 3,577,458 A | 5/1971 | Brownstein et al. |
| 3,656,906 A | 4/1972 | Bullock |
| 3,838,131 A | 9/1974 | Gauthier et al. |
| 3,886,184 A | 5/1975 | Matsumoto et al. |
| 3,897,306 A | 7/1975 | Vidic |
| 3,915,996 A | 10/1975 | Wright |
| 3,928,598 A | 12/1975 | Archer |
| 3,944,673 A | 3/1976 | Archer |
| 3,953,603 A | 4/1976 | Archer |
| 4,036,857 A | 7/1977 | Razdan et al. |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan et al. |
| 4,176,233 A | 11/1979 | Archer et al. |
| 4,179,517 A | 12/1979 | Mechoulam |
| 4,188,495 A | 2/1980 | Althuis et al. |
| 4,208,351 A | 6/1980 | Archer et al. |
| 4,278,603 A | 7/1981 | Thakkar et al. |
| 4,282,248 A | 8/1981 | Mechoulam et al. |
| 4,382,943 A | 5/1983 | Winter et al. |
| 4,395,560 A | 7/1983 | Ryan |
| 4,497,827 A | 2/1985 | Nelson |
| 4,550,214 A | 10/1985 | Mehta |
| 4,758,597 A | 7/1988 | Martin et al. |
| 4,812,457 A | 3/1989 | Narumiya |
| 4,876,276 A | 10/1989 | Mechoulam |
| 4,885,295 A | 12/1989 | Bell et al. |
| 5,053,548 A | 10/1991 | Tanaka et al. |
| 5,068,234 A | 11/1991 | D'Ambra et al. |
| 5,147,876 A | 9/1992 | Mizuchi et al. |
| 5,223,510 A | 6/1993 | Gubin et al. |
| 5,284,867 A | 2/1994 | Kloog |
| 5,324,737 A | 6/1994 | D'Ambra et al. |
| 5,434,295 A | 7/1995 | Mechoulam et al. |
| 5,440,052 A | 8/1995 | Makriyannis et al. |
| 5,462,960 A | 10/1995 | Barth et al. |
| 5,489,580 A | 2/1996 | Makriyannis et al. |
| 5,521,215 A | 5/1996 | Mechoulam |
| 5,532,237 A | 7/1996 | Gallant et al. |
| 5,538,993 A | 7/1996 | Mechoulam |
| 5,576,436 A | 11/1996 | McCabe et al. |
| 5,605,906 A | 2/1997 | Lau |
| 5,607,933 A | 3/1997 | D'Ambra et al. |
| 5,618,955 A | 4/1997 | Mechoulam et al. |

(Continued)

FOREIGN PATENT DOCUMENTS

EP    0471609    6/1993

(Continued)

OTHER PUBLICATIONS

U.S. Appl. No. 09/600,786, filed Nov. 24, 1999, Makriyannis et al (copy not included, this is the U.S. National Phase of the Int'l Application published as WO 00/32200 enclosed herewith).

(Continued)

*Primary Examiner*—Charanjit S. Aulakh
(74) *Attorney, Agent, or Firm*—Alix, Yale & Ristas, LLP

(57) ABSTRACT

Novel tricyclic cannabinoid compounds are presented. Some of these compounds exhibit fluorescence properties. The fluorescent cannabinoid compounds are typically endogenously fluorescent. Some of these compounds, when administered in a therapeutically effective amount to an individual or animal, result in a sufficiently high level of that compound in the individual or animal to cause a physiological response. The physiological response useful to treat a number of physiological conditions.

15 Claims, No Drawings

U.S. PATENT DOCUMENTS

| | | | |
|---|---|---|---|
| 5,624,941 | A | 4/1997 | Barth et al. |
| 5,635,530 | A | 6/1997 | Mechoulam |
| 5,688,825 | A | 11/1997 | Makriyannis et al. |
| 5,744,459 | A | 4/1998 | Makriyannis et al. |
| 5,747,524 | A | 5/1998 | Cullinan et al. |
| 5,804,601 | A | 9/1998 | Kato et al. |
| 5,817,651 | A | 10/1998 | D'Ambra et al. |
| 5,872,148 | A | 2/1999 | Makriyannis et al. |
| 5,874,459 | A | 2/1999 | Makriyannis et al. |
| 5,925,628 | A | 7/1999 | Lee et al. |
| 5,925,768 | A | 7/1999 | Barth et al. |
| 5,932,610 | A | 8/1999 | Shohami et al. |
| 5,948,777 | A | 9/1999 | Bender et al. |
| 6,013,648 | A | 1/2000 | Rinaldi et al. |
| 6,028,084 | A | 2/2000 | Barth et al. |
| 6,096,740 | A | 8/2000 | Mechoulam |
| 6,127,399 | A | 10/2000 | Yuan |
| 6,166,066 | A | 12/2000 | Makriyannis et al. |
| 6,284,788 | B1 | 9/2001 | Mittendorf et al. |
| 6,391,909 | B1 | 5/2002 | Makriyannis et al. |
| 6,579,900 | B2 | 6/2003 | Makriyannis et al. |
| 6,610,737 | B1 | 8/2003 | Garzon et al. |
| 2002/0119972 | A1 | 8/2002 | Leftheris et al. |
| 2003/0120094 | A1 | 6/2003 | Makriyannis et al. |
| 2003/0149082 | A1 | 8/2003 | Makriyannis et al. |
| 2004/0077649 | A1 | 4/2004 | Markiyannis et al. |
| 2004/0077851 | A1 | 4/2004 | Makriyannis et al. |
| 2004/0087590 | A1 | 5/2004 | Makriyannis et al. |

FOREIGN PATENT DOCUMENTS

| | | |
|---|---|---|
| EP | 0737671 | 10/1996 |
| EP | 0860168 | 9/2001 |
| FR | 2240003 | 5/1975 |
| FR | 2735774 | 1/2000 |
| GB | 2027021 A | 2/1980 |
| JP | 57098228 | 6/1982 |
| WO | WO 97/00860 | 1/1997 |
| WO | WO 99/57107 | 11/1999 |
| WO | WO 99/64389 | 12/1999 |
| WO | WO 00/32200 | 6/2000 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/32169 | 5/2001 |
| WO | WO 01/58869 | 8/2001 |
| WO | WO 03/005960 | 1/2003 |
| WO | WO 03/020217 | 3/2003 |
| WO | WO 03/035005 | 5/2003 |
| WO | WO 03/063758 | 8/2003 |
| WO | WO 03/064359 | 8/2003 |

OTHER PUBLICATIONS

U.S. Appl. No. 09/701,989, filed Jun. 9, 1999, Makriyannis et al (copy not included, this is the U.S. National Phase of the Int'l Application published as WO 99/64389 enclosed herewith).

U.S. Appl. No. 10/110,865, filed Oct. 18, 2000, Makriyannis et al (copy not included, this is the U.S. National Phase of the Int'l Application published as WO 01/28497 enclosed herewith).

U.S. Appl. No. 10/110,830, filed Oct. 18, 2000, *1* Makriyannis et al (copy not included, this is the U.S. National Phase of the Int'l Application published as WO 01/28329 enclosed herewith).

U.S. Appl. No. 10/110,812, filed Oct. 18, 2000, Makriyannis et al (copy not inlcuded, this is the U.S. National Phase of the Int'l Application published as WO 01/28498 enclosed herewith).

U.S. Appl. No. 10/110,862, filed Oct. 18, 2000, Makriyannis et al (copy not included, this is the U.S. National Phase of the Int'l Application published as WO 01/29007 enclosed herewith).

U.S. Appl. No. 10/111,059, filed Oct. 18, 2000, Makriyannis et al (copy not included, this is the U.S. National Phase of the Int'l Application published as WO 01/28557 enclosed herewith).

U.S. Appl. No. 10/483,482, filed Jul. 11, 2002, *1* Makriyannis et al (copy not included, this is the U.S. National Phase of the Int'l Application published as WO 03/005960 enclosed herewith).

U.S. Appl. No. 10/493,093, filed Oct. 28, 2002, Makriyannis et al (copy not included, this is the U.S. National Phase of the Int'l Application published as WO 03/35005 enclosed herewith).

U.S. Appl. No. 10/790,498, filed Mar. 1, 2004, Makriyannis et al. Abadji V., Lin S., Taha G., Griffin G., Stevenson L.A., Pertwee R.G., Makriyannis A.; "(R)-Methanadamide: a chiral novel anandamide possessing higher potency and metabolic stability"; J. Med. Chem.; 37(12); 1889-1893; 1994; CODEN: JMCMAR; ISSN: 0022-2623; XP002040932.

*1* Alo, B.I.; Kandil, A.; Patil, P. A.; Sharp, M. J.; Siddiqui, M. A.; and Snieckus, V. Sequential Directed Ortho Metalation-Boronic Acid Cross-Coupling Reactions. A general Regiospecific Route to Oxygenerated Dibenzo[b,d]pyran-6-ones Related to Ellagic Acid, J. Org. Chem. 1991, 56, 3763-3768.

*** Archer et al; "Cannabinoids, synthesis approaches to 9-ketocannabinoids."; J. Org. Chem.; vol. 42; No. 13; 2277-2284; (1977).

*1* Arnone M., Maruani J., Chaperon P, et al, Selective inhibition of sucrose and ethanol intake by SR141716, an antagonist of central cannabinoid (CB1) receptors, Psychopharmacal, (1997) 132, 104-106. (abstract only).

*1* Barnett-Norris et al; "Exploration of biologically relevant conformations of anandamide, . . . "; J. Med. Chem.; vol. 41; 4861-4872; 1998.

*1* Beak, P.; and Brown, R A., The Tertiary Amide as an Effective Director of Ortho Lithiation, J. Org. Chem. 1982, 47, 34-36.

*1* Belgaonkar et al; "Synthesius of isocoumarins"; Indian J. Chem; vol. 13; No. 4; 336-338; 1975 (abstract only).

Beltramo M., Stella N., Calignano A., Lin S. Y., Makriyannis A., Piomelli D; "Functional Role Of High-Affinity Anandamide Transport, as Revealed By Selective Inhibition"; Science; vol. 277; 1094-1097; 1997.

Beltramo M., Stella N., Calignano A., Lin S. Y., Makriyannis A., Piomelli D; "Identification and Functional Role of High Affinity Anandamide Transport"; The Neurosciences Institute (1 page).

Berdyshev EV, Cannabinoid receptors and the regulation of immune response. Chem Phys Lipids. Nov. 2000; 108(1-2):169-90.

Berglund et al; "Structural requirements for arachidonylethanolamide interaction with CB1 and CB2 cannabinoid receptors: . . . "; Prostanglandins, leukotrienes ands essential fatty acids; 59(2); 111-118; (1998). (abstract only).

Bodnar, V.N., Lozinskii, M.O., Pel'kis, P.S.; "Synthesis fo 2,5-disubstituted 1,3,4-oxadiazoles and 1,4-dihydro-1,2,4,5-tetrazines"; Ukrainskii Khimicheskii Zhurnal (Russian Edition); 48(12); 1308-1311; 1982 (abstract only).

Bracey, M et al, Structural Adaptations in a Membrane Enzyme That Terminates Endocannabinoid Signaling. Science 2002; 298(5599): 1793-1796.

*1* Brenneisen R, Pgli A, Elsohly MA, Henn V. Spiess Y: The effect of orally and rectally administered 9-tetrahydrocannabinol on spasticity, a pilot study with 2 patients. Int. J. Clin Pharmacol Ther. (1996) 34:446-452. (abstract only).

*1* *** Brotchie JM: *Adjuncts to dopamine replacement a pragmatic approach to reducing the problem of dyskinesia in Parkinson's disease. Mov. Disord.* (1998)13:871-876.

*1* Brown et al; "Synthesis and hydroboration of (-)-2-phenylapopinene, Comparison of mono(2-phenylapoisopinocampheyl)borane with its 2-methyl and 2-ethyl analogues for the chiral hydroboration of representative alkenes"; J. Org. Chem.; 55(4); 1217-1223; (1990).

*1* Buckley NE, McCoy KI, Mpzey E et al, "Immunomodulation by cannabinoids is absent in mice deficient for the cannabinoid CB2 receptor"; Eur. J Pharmacol (2000) 396:141-149.

*1* Burstein et al; "Detection of cannabinoid receptors . . . "; Biochem. Biophys. Res. Commun.; vol. 176(1); 492-497; 1991 (abstract only).

Busch-Peterson et al; "Unsaturated side chain beta-11-hydroxyhexahydrocannabinol analogs"; J. Med. Chem.; 39; 3790-3796; (1996).

*1* Calignano A, La Rana G. Diuffrida A, Piomelli D; "Control of pain initiation by endogenous cannabinoids"; Nature (1998) 394:277-291. (abstract only).

Calignano A., La Rana G., Beltramo, M., Makriyannis A., Piomelli D; "Potentiation of Anandamide Hypotension by the Transport Zinhibitor, AM404"; Eur. J. Pharmacol.; 1997; 337 R1-R2.

Calignano A., La Rana G., Makriyannis A., Lin. S., Beltramo M., Piomelli D; "Inhibition of Intestinal Motility by Anandamide, an Endogenous Cannabinoid"; Eur. J. Pharmacol.; 1997; 340 R7-R8.

Campbell FA et al; "Are cannabinoids an effective and safe treatment option in the management of pain? A qualitative systematic review"; BMJ. Jul. 7, 2001;323(7303):13-6.

*1* Charalambous A. et al; "5'-azido 8-THC: A Novel Photoaffinity Label for the Cannabinoid Receptor"; J. Med. Chem., 35, 3076-3079 (1992).

*1* Charalambous A. et al; "Pharmacological evaluation of halogenated . . . "; Pharmacol. Biochem. Behav.; vol. 40; No. 3; 509-512; 1991.

*1* Cheng et al; "Relationship Between the Inhibition Constant (Ki) and the concentration of Inhibitor which causes 50% Inhibition (IC50) of an Enzymatic Reaction"; Biochem. Pharmacol., 22, 3099-3102, (1973) (abstract only).

Cherest M., Luscindi X.; "The action of acetyl chloride and of acetic anhydride on the lithium nitronate salt of 2-phenylnitroethane . . . "; Tetrahedron; 42(14); 3825-3840; 1986; in French with English abstract.

Cherest M., Lusinchi X.; "A novel electrophilic N-amidation via electron deficient complexes: action of ferric chloride on N-acetyloxyamides"; Tetrahedron Letters; 30(6); 715-718; 1989.

*1* Colombo G, Agabio R, Diaz G. et al; "Appetite suppression and weight loss after the cannabinoid antagonist SR141716"; Life Sci. (1998) 63-PL13-PL117. (abstract only).

*** Compton D.R. et al; J. Pharmacol. Exp. Ther.; 260; 201-209; 1992.

*1* Compton et al; "Synthesis and pharmacological evaluation of ether and related analogues of delta8-, delta9- and delta9,11-tetrahydrocannabinol"; J. Med. Chem; vol. 34; No. 11; 3310-3316; 1991.

*1* Consroe P, Musty R, Rein J, Tillery W, Pertwee R; "The perceived effects of smoked cannabis on patents with multiple sclerosis"; Eur. Neurol. (1997) 38-44-48. (abstract only).

Coxon et al; "Derivatives of nopinone"; Aust. J. Chem.; 23; 1069-1071; (1970) (abstract only).

*1* Crawley et al; "Anandamide, an endogenous ligand of the cannabinoid receptor, induces hypomotility and hypothermia in vivo in rodents"; Pharmacology Biochemistry and Behavior; vol. 46; 967-972; 1993.

D'Ambra et al; "C-attached aminoalkylindoles: potent cannabinoid mimetics"; Bioorg. & Med. Chem. Lett., 1996, 6(1), 17-22.

*** D'Amour F.E., Smith D.L.; J. Pharmacol. Exp. Ther.; 72; 74-79; 1941.

Demuynck L. et al; "Rearrangement of Indolo[2,3-a]quinolizidines to derivatives with E-azaaspidospermane skeleton"; Tetrahedron Letters; 30(6) 710-722; 1989; in French with English abstract.

*1* DePetrocellis L, Melck D, Palmisano A. et al; "The endogenous cannabinoid anandamide inhibits human breast cancer cell proliferation"; Proc. Natl. Acad. Sci. USA (Jul. 1998) 95:8375-8380.

Desarnaud F., Cadas H., Piomelli D.; "Anandamide amidohydrolase activity in rat brain microsomes"; J. Biol. Chem.; 270; 6030-6035; (1995).

Deutsch D.G. et al; "Fatty acid sulfonyl fluorides inhibit anandamide metabolism and bind to cannabinoid receptor"; Biochem. Biophys. Res. Commun. 231(1); 217-221; 1997; CODEN: BBRCA9; ISSN:0006-291X; XP002040933.

Deutsch D.G., Chin S.A.; "Enzymatic synthesis and degradation of anandamide, a cannabinoid receptor agonist"; Biochemical Pharmacology; 46(5); 791-796; 1993.

*1* Devane, W.A. et al; "Determination and Characterization of a Cannabinoid Receptor in a Rat Brain"; Mol. Pharmacol., 34, 605-613 (1988). (abstract only).

*1* Di Marzo, V., Melck, D., Bisogno, T., DePetrocellis, L.; "Endocannabinoids: endogenous cannabinoid receptor ligands with neuromodulatory action"; Trends Neurosci. (1998) 21:521-528.

*** Dodd, P.R. et al, *A Rapid Method for Preparing Synaptosomes: Comparison with Alternative Procedures, Brain Res.*, 226, 107-118 (1981).

*1* Dominiami et al; "Synthesis of 5-(tert-Alkyl)resorcinols"; J. Org. Chem. 42(2); 344-346; (1977).

Drake et al, "Classical/nonclassical hybrid cannabinoids"; J. Med. Chem.; vol. 41(19); 3596-3608 (1998).

Edery et al; "Activity of novel aminocannabinoids in baboons"; J. Med. Chem.; 27; 1370-1373 (1984).

Eissenstat et al; "Aminoalkylindoles: structure-activity relationships of novel cannabinoid mimetics"; J. Med. Chem. 1995, vol. 38, No. 16, pp. 3094-3105; XP 000651090.

Fahrenholtz, K. E., Lurie, M. and Kierstead, AR. W.; "The Total Synthesis of dl-$\Delta$9-Tetrahydrocannabinol and Four of Its Isomers"; J. Amer. Chem. Soc. 1967, 89(23), 5934-5941.

*1* Fahrenholtz; "The synthesis of 2 metabolites of (-)-delta eight-tetrahydrocannabinol"; J. Org. Chem.; vol. 37(13); 1972; XP002111824.

Fisera, L., Kovac J., Lesco, J., Smahovsky, V.; "Furan derivatives. Part CLVI. 1,3-dipolar cycloadditions of heterocycles. V. Reaction of C-acetyl-N-phenylnitrilimine with furan derivatives"; Chemicke Zvesti; 35(1); 93-104 1981 (abstract only).

*1* Fride, E. & Mechoulam, R.; "Pharmacological activity of the cannabinoid receptor agonist, anandamide, a brain constituent"; European Journal of Phamacology, vol. 231; 313-314; 1993.

Galiegue S et al. ; "Expression of central and peripheral cannabinoid receptors in human immune tissues and leukocyte subpopulations"; Eur J Biochem.; Aug. 15, 1995;232(1):54-61. (abstract only).

*1* Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189-194.

*1* Gold et al; "A comparison of the discriminative stimulus properties of delta9-tetrahydrocannabinol and CP 55,940 in rats and rhesus monkeys"; J. Pharmacol. Exp. Ther.; vol. 262(2); 479-486; 1992.

*1* *** Green K. Marijuana smoking vs. cannabinoids for glaucoma therapy. *Arch. Ophibalmol.* (1998) Feb. 433-1437.

*1* Hampson, A.J., Grimaldi M. Axpirod J. Wink D; "Cannabidiol and (-) 9 tetrahydrocannabinol are neuroprotective antioxidants"; Proc. Natl Acad Sci. USA (Jul. 1998) 95; 8268-8273.

*1* Hargreaves, K. et al; "A new sensitive method for measuring thermal nociception in cutaneous hyperalgesia"; Pain; 32; 77-88; (1988) (abstract only).

*1* *** Hemming M, Yellowlees PM; "Effective treatment of Tourette's syndrome with marijuana"; *J. Psychopharmacol*, (1993) 7:389-391.

*1* Herzberg U, Eliav E, Bennett GJ, Kopin IJ; "The analgesic effects of R(+) WIN 55,212-2 mesylate, a high affinity cannabinoid agonist in a rat model of neuropathic pain"; Neurosci. Letts. (1997) 221; 157-160.

Hillard C. J., Edgemond, W. S., Jarrahian W., Campbell, W. B; "Accumulation of N-Arachidonoylethanolamine (Anandamide) into Cerebellar Granule Cells Occurs via Facilitated Diffusion"; Journal of Neurochemistry; 69; 631-638 (1997).

Horrevoets A.J.G et al; "Inactivation of *Escherichia coli* outer membrane phospholipase A by the affinity label hexadecanesulfonyl fluoride"; Eur. J. Biochem.; 198; 247-253; 1991.

Horrevoets A.J.G et al; "Inactivation of reconstituted *Escherichia coli* outer membrane phospholipase A by membrane-perturbing peptides results in an increased reactivity towards the affinity label hexadecanesulfonyl fluoride"; Eur. J. Biochem.; 198; 255-261; 1991.

Howlett et al; "Azido and isothicyanato substituted aryl pyrazoles bind covalently to the CB1 cannabinoid receptor and impair signal transduction"; Journal of Neurochemistry; vol. 74(5) (2000) 2174-2181; XP001097394.

*1* Howlett et al; "Stereochemical effects of 11-OH-delta 8 tetrahydrocannabinol-dimethylheptyl to inhibit adenylate cyclase and bind to the cannabinoid receptor"; Neuropharmacology; vol. 29(2); 161-165; 1990.

Huffman et al; "3-(1',1'-dimethylbutyl)—deoxy-delta 8THC and related compounds: synthesis of selective ligands for the CB2 receptor"; Bioorganic and Medicinal Chemistry; vol. 7; 2905-2914; (1999).

Huffman et al; "Stereoselective synthesis of the epimeric delta 7-tetrahydocannabinols"; tetrahedron; vol. 51(4); 1017-1032; (1995).

*1* Huffman et al; "Synthesis of 5',11 dihydroxy delta 8 tetrahydrocannabinol"; Tetrahedron, vol. 53(39), pp. 13295-13306 (1997).

*1* Huffman et al; "Synthesis of a tetracyclic, conformationally constrained analogue of delta8-THC"; Bioorganic & Medicinal Chemistry; vol. 6(12); 2281-2288; 1998; XP002123230.

*1* Huffman et al; "Synthesis of both enantiomers of Nabilone from a common intermediate. Enantiodivergent synthesis of cannabinoids"; J. Org. Chem.; 1991, 56, 2081-2086.

*1* *** Joy JE, Wagtson SJ, Benson JA; "Marijuana and Medicine Assessing the Science Base"; *National Academy Press*, Washington, DC, USA (1999).

Kaminski NE; "Regulation of the cAMP cascade, gene expression and immune function by cannabinoid receptors"; J Neuroimmunol. Mar. 15, 1998;83(1-2):124-32.

Kawase M. et al; "Electrophilic aromatic substitution with N-methoxy-N-acylnitrenium ions generated from N-chloro-N-methoxyamides: synthesis of nitrogen heterocyclic compounds bearing a N-methoxyamide group"; J. Org. Chem.; 54; 3394-3403; 1989.

Khanolkar A., Abadji V., Lin S., Hill W., Taha G., Abouzid K., Meng Z., Fan P., Makriyannis A.; "Head group analogues of arachidonylethanolamide, the endogenous cannabinoid ligand"; J. Med. Chem.; vol. 39(22); 4515-4519; (1996).

Khanolkar et al; "Molecular probes for the cannabinoid receptors"; Chemistry and Physics of Lipids; 108; 37-52; (2000).

Klein T.W. et al, "The cannabinoid system and cytokine network"; Proc Soc Exp Biol Med. Oct. 2000; 225(1):1-8; (abstract only).

Klein TW et al, "Cannabinoid receptors and immunity"; Immunol Today; Aug. 1998; 19(8):373-81.

Koutek B. et al; "Inhibitors of arachidonyl ethanolamide hydrolysis"; J. Biol. Chem.; 269(37); 22937-40; 1994; CODEN: JBCHA3; ISSN: 0021-9258; XP002040931.

Kumar RN, et al; "Pharmacological actions and therapeutic uses of cannabis and cannabinoids"; Anesthesia, 2001, 56: 1059-1068 (abstract only).

Lan, R et al; "Structure activity relationships of pyrazole derivatives as cannabinoid receptor antagonists"; J. Med. Chem.; vol. 42(4); 769-776; (1999).

*1* Lavalle et al; "Efficient conversion of (1R, 5R)-(+)-alpha-pinene to (1S, 5R)-(-)-nopinene"; J. Org. Chem.; vol. 51(8); 1362-1365; (1986).

Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

*1* Loev, B., Bender, P. E., Dowalo, F., Macko E., and Fowler, P.; "Cannabinoids. Structure-Activity Studies Related to 1,2-Dimethylheptyl Derivatives"; J. Med. Chem.; vol. 16(11); 1200-1206; 1973.

Lozinskii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635-2637; 1990 (abstract only).

*1* Ludt, R.E. et al; "A comparison of the synthetic utility of n-butyllithium and lithium diisopropylamide in the metalations of N,N-dialkyltouamides"; J. Org. Chem.; 38(9); 1668-1674 (1973).

*** Maccarron M., Endocannabinoids and their actions. *Vitamins and Hormones* 2002;65:225-255.

Mackie K., Devane W.A., Hille B.; "Anandamide, an endogenous cannabinoid, inhibits calcium currents as a partial agonist in N18 neuroblastoma cells"; Mol. Pharmacol; 44; 498-0503 (1993).

*1* *** Markwell et al; *Anal. Biochem.*; 87:206 (1978).

*1* Martin et al; "Behavioral, biochemical, and molecular modeling evaluations of cannabinoid analogs"; Pharmacol. Biochem. Behav.; vol. 40(3); 471-478; 1991.

*1* Martyn CN. Illis LS, Thom J.; "Nabilone in the treatment of multiple sclerosis"; Lancet (1995) vol. 345; pp. 579.

*1* Matsumoto et al; "Cannabinoids 1.1-amino-and 1 mercapto-7,8,9,10-tetrahydro-6h-dibenzo[b,d]pyrans"; J. of Med. Chem.; vol. 20(1); 17-24; 1977; XP00211825.

*1* *** Maurer M, Henn V, Dittrich A, Hofmann A. Delta-9-tetrahydrocannabinol shows antispastic and analgesic effects in a single case double-blind trial. *Eur. Arch. Psychiat. Clin. Neurosci.* (1990), Z40:1-4.

*1* Mavromoustakos, T. et al; "Studies on the thermotropic effects of cannabinoids on phosphatidylcholine bilayers using differential scanning calorimetry and small angle X-ray diffraction"; Biochimica et Biophysica Acta; vol. 1281(2); 1996; XP002111823.

Mechoulam et al; "Stereochemical Requirements for cannabinoid activity"; J. Med. Chem.; 23(10); 1068-1072; (1980).

Mechoulam et al; "Synthesis of the individual, pharmacologically distinct, enantiomers of a tetrahydrocannabinol derivative"; Tetrahedron Asymmetry; 1: 311-314; (1990) (abstract only).

*** Mechoulam et al; *Tetrahedron Asymmetry*; 1: 315-318; (1990).

*1* *** Mechoulam, "Cannabinoids as therapeutic agents"; *CRC press*, 1986.

*1* Meltzer et al; "An improved synthesis of cannabinol and cannabiorcol"; Synthesis; 1981:985 (1981).

*** Melvin et al; *Drug design and discovery*; 13; 155-166 (1995).

Melvin et al; "Structure-activity relationships for cannabinoid receptor-binding and analgesic activity: studies of bicyclic cannabinoid analogs"; Mol. Pharmacol.; 44(5); 1008-1015 (1993).

*1* Merck Index; 11th edition; "Tetrahydrocannabinols" compound No. 9142; 1989.

*1* *** Morgan Dr: Therapeutic Uses of Cannabis. *Harwood Academic Publishers*, Amsterdam. (1997).

*1* *** Morris, S,; Mechoulam, R.; and Irene, Y., *Halogenation of phenols and Phenyl ethers with Potassium Halides in the Presence of 18-Crown-6 on Oxidation with m-Choloroperbenzoic Acid, J. Chem. Soc., Perkin Trans.* 1 1987, 1423-1427.

*1* *** Muller-Vahl KB, Kolbe H, Schneider U, Emrich, HM *Cannabis in movement disorders. Porsch. Kompicmentarmed* (1999) 6 (suppl. 3) 23-27.

*1* *** Muller-Vahl KB, Schneider U, Kolbe H, Emrich, HM. Treatment of Tourette's syndrome with delta-9-tetrahydrocannabinol. *Am. J. Psychiat.* (1999) 156-195.

*** Nahas G, Marijuana and Medicine; 1999, *Human Press Inc.*, Totowa, NJ.

Neunhoeffer O., Gottschlich R.; "Acylating activity of O-acylated hydroxylamine derivatives"; Justus Liebigs Ann. Chem.; 736; 100-109; 1970; in German with English abstract.

*1* Novak, J et al; Cannabis, part 27, synthesis of 8-, 10- and 11-oxygenated cannabinoids; J. Chem. Soc. Perkin Trans.; 2867-2871; (1983) (abstract only).

*1* Nye et al; "High affinity cannabinoid binding sites in brain membranes labelled with [H]-5'-trimethylammonium delta8-tetrahydrocannabinol"; J. Pharmacol. Exp. Ther.; vol. 234(3); 784-791; 1985.

*** Palmer et al; *Current pharmaceutical design*; 6; 1381-1397; (2000).

*1* Papahatjis et al; "A new ring-forming methodology for the synthesis of conformationally constrained bioactive molecules"; Chemistry Letters, 192; (2001).

*1* Papahatjis et al; "Pharmacophoric requirements for cannabinoid side chains: multiple bond and C1'-substituted delta8-tetrahydrocannabinols"; J. Med. Chem.; 41(7); 1195-1200; (1998).

Pertwee et al; "AM630, a competitive cannabinoid receptor agonist"; Life Sci. 1995, 56(23/24), 1949-1955; XP 000653566.

Pertwee et al; "Pharmacological characterization of three novel cannabinoid receptor agonists in the mouse isolated vas deferens"; Eur. J. Pharmacol. 1995, 284, 241-247; XP-001041044.

\*\*\* Pertwee et al; *Br. J. Pharmacol.*; 105; 980 1992.

\*1\* Pertwee; Pharmacology of cannabinoid CB1 and CB2 receptors; Pharmacol. Ther., vol. 74(2); pp. 129-180; (1997); XP002226467.

Petrov, M.L., Terent'eva, N.A., Potekhin, K.A., Struchkov, Yu. T.; ".alpha.,.beta.-unsaturated thiolates and their analogs in cycloaddition reactions. XVIII. Reaction of (2-phenylethynyl)tellurolates with C-ethoxycarbonyl-N-Phenylnitrilimine"; Zhurnal Organicheskoi Khimii; 29(7); 1372-1378; (1993) (abstract only).

\*1\* \*\*\* Pinnegan-Ling D, Musty R.; Marinol and phantom limb pain: a case study. Proc Inv. Cannabinoid Rea. Sec. (1994):53.

Piomelli D., Beltramo M., Glasnapp S., Lin S.Y., Goutopoulos A., Xiw X-Q., Makriyannis A.; "Structural determinants for recognition and translocation by the anandamide transporter"; Proc. Natl. Acad. Sci. USA; 96: 5802-5807; (1999).

\*1\* Pitt et al; "The synthesis of Deuterium, carbon-14 and carrier free tritium labelled cannabinoids"; Journal of Labelled Compounds; vol. 11(4); 551-575; 1975; XP002123229.

\*\*\* Porreca F., Mosberg H.I., Hurst R., Hruby V.J., Burks T.F.; "Roles of mu, delta and kappa opiod receptors in spinal and supraspinal mediation of gastrointestinal transit effects and hot-plate analgesia in the mouse"; *J. Pharmacol. Exp. Ther.*; 230; 341-348; (1994).

\*1\* Razdan et al; "Drugs delivered from cannabinoids. 6. .Synthesis of cyclic analogues of dimethylheptylpyran"; J. Med. Chem.; vol. 19(5); 719-721; 1976 (abstract only).

\*1\* Reggio et al; "Characterization of a region of steric interference at the cannabinoid receptor using the active analog approach"; J. Med. Chem. United States; vol. 36(12); 1761-1771; 1993.

\*1\* Rhee, M. H.; Vogel, Z.; Barg, J.; Bayewitch, M.; Levy, R.; Hanus, L.; Breuer, A.; And Mechoulam, R.; "Cannabinoid Derivatives: Binding to Cannabinoid Receptors and Inhibition of Adenylcyclase"; J. Med. Chem. 1997, 40(20); 3228-3233.

\*\*\* Rice AS. Cannabinoids and pain. *Curr Opin Investig Drugs.* Mar. 2001;2(3):399-414.

\*1\* Richardson JD, Aanonsen I, Hargreaves KM; "Antihyperalgesic effects of a spinal cannabinoids"; Eur. J. Pharmacol. (1998) 346:145-153.

\*1\* Richardson JD, Kilo S. Hargreaves KM; "Cannabinoids reduce dryperalgesia and inflammation via interaction with peripheral CB1 receptors"; Pain (1998) 75:111-119.

Rinaldi-Carmona et al; "Biochemical and pharmacological characterization of SR141716A, the first potent and selective brain cannabinoid receptor antagonist"; Life Sci.; vol. 56(23/24); 1941-1947 (1995).

Rinaldi-Carmona et al; "SR141716A, a potent and selective antagonist of the brain cannabinoid receptor"; FEBS Lett.; 350; 240-244; (1994).

\*1\* Rompp Chemie Lexikon; Falbe and Regitz; "Band 1-A-C1, 8"; Aufl, Thieme Verlag; Stuttgart, S 569-570; 1989.

Santus, Maria; "Studies on thioamides and their derivatives. IX. Synthesis of the derivatives of 1,2,4,5-tetrazine"; Acta Polonae Pharmaceutica; 50(2-3); 183-188; 1993 (abstract only).

Schatz AR et al; "Cannabinoid receptors CB1 and CB2: a characterization of expression and adenylate cyclase modulation within the immune system"; Toxicol Appl Pharmacol. Feb 1997; 142(2):278-87.

\*1\* \*\*\* Schuel, H., Burkman, L.J., Picone, R.P., Bo, T., Makriyannis, A., Cannabinoid receptors in human sperm. *Mol. Biol. Cell.*, (1997) (8), 325a.

\*\*\* Serdarevich B., Caroll K.K., "Synthesis and characterization of 1- and 2-monoglycerides of anteiso fatty acids"; *J. Lipid Res.*; 7; 277-284; (1966).

Shawali, A.S., Albar, H.A.; "Kinetics and mechanism of dehydrochlorination of N-aryl-C-ethoxycarbonyl formohydrazidoyl chlorides"; Canadian Journal Of Chemistry; 64(5); 871-875; 1986 (abstract only).

\*1\* \*\*\* Shen M. Thayer SA: Cannabinoid receptor agonists protect cultured rat hippocampal neurons from excitotoxicity. *Mol. Pharmacol* (1996) 54:459-462.

Shim et al; "Three-dimensional quantitative structure-activity relationship study of the cannabimimetic (aminoalkyl)indoles using comparative molecular field analysis"; J. Med. Chem.; 1998, 41(23); 4521-4532; XP-002212407.

Shim et al; "Unified pharmacophoric model for cannabinoids and aminoalkylindoles derived from molecular superimposition of CB1 cannabinoid receptor agonists CP55244 and WIN55212-2"; ACS Symposium series, 1999 719 (rational drug design), 165-184; XP-001095771.

Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989-999; XP-001097918.

\*1\* \*\*\* Simiand J, Keane M, Keane PE, Soubrie P: SR 141716, A CB1 cannabinoid receptor antagonist, selectively reduces sweet food intake in marmoset. *Behav. Pharmacol* (1998) 9:179-181.

\*1\* Smith P.B. et al; "The pharmacological activity of anandamide, a putative endogenous cannabinoid, in mice"; Journal of Pharmacology and Experimental Therapeutics; vol. 270(1):219-227; 1994.

\*1\* \*\*\* Terranova J-P, Storme J-J Lafon N et al; "Improvement of memory in rodents by the selective CB1 cannabinoid receptor antagonist, SR 141716"; *Psycho-pharmacol* (1996) 126:165-172.

Tius et al; "Conformationally restricted hybrids of CP-55,940 and HHC: Steroeselective synthesis and activity"; Tetrahedron; 50 (9); 2671-2680; (1994) (abstract only).

Twitchell, W. et al; "Cannabinoids inhibit N- and P/Q type calcium channels in cultured rat hippocampal neurons"; Journal of Neurophysiology; 78(1); 43-50; 1997 (abstract only).

\*\*\* Ueda, N., *Endocannabinoid hydrolases. Prostaglandins & Other Lipid Mediators 2002*; 68-69:521-534.

\*\*\* Vogel Z., Barg J., Levy R., Saya D., Heldman E., Mechoulam R.; "Anandamide, a brain endogenous compound, interacts specifically with cannabinoid receptors and inhibits adenylate cyclase"; *J. Neurochem.*; 61(1) 352-355; (1993).

\*1\* \*\*\* Wagner JA, Varga K, Jarai Z, Kunos G; 'Mesenteric vasodialtion mediated by endothelia anandamide receptors'; *Hypertension* (1999) 33:429-434.

\*1\* Watanabe, T.; Miyaura, N.; and Suzuki, A.; "Synthesis of Sterically Hindered Biaryls via the Palladium Catalyzed Cross-Coupling Reaction of Arylboronic Acids or their Esters with Haloarenes"; Synlett 1992, 207-210.

Wiley et al; "Structure activity relationships of indole and pyrrole derived cannabinoids"; J. Pharmacol. Exp. Ther. 1998, 285(3), 995-1004; XP-001097982.

Wilson et al; "9-nor-delta8-tetrahydrocannabinol, a cannabinoid of metabolic intersts"; J. Med. Chem.; 17(4); 475-476; (1974).

Wilson et al; "Analgesic properties of the tetrahydrocannabinols, their metabolites and analogs"; J. Med. Chem.; 18(7); 700-703; (1975).

Wilson et al; "9-nor-9-hydrohexahydrocannabinols. Synthesis, some behavioral and analgesic properties, and comparison with the tetrahydrocannabinols"; J. Med. Chem.; 19(9); 1165-1167; (1976).

Yamada et al; "(Aminoalkyl)indole isothiocyanates as potentiual electrophilic affinity ligands for the brain cannabinoid receptor"; J. Med. Chem. 1996, vol. 39(10), 1967-1974.

Yan, Guo et al; "Synthesis and pharmacological properties of 11-hydroxy-3-(1'-1'-dimethylheptyl)hexahydrocannabinol: a high affinity cannabinoid agonist"; J. Med. Chem.; vol. 37(16); 2619-2622; (1994).

\*1\* Yan Guo et al; "(-)-11-hydroxy-7'-isothiocyanato-1'-1'dimethylheptyl-delta8-THC: a novel probe for the cannabinoid receptor in the brain"; J. Med. Chem.; 37(23); 3867-3870; (1994).

Database CAPLUS on STN, AN 1991: 679813, Nakayama et al. "Preparation of 6H-dibenzo[b,d]pyran-6-ones and their use as aldoes reductase inhibitors", Abstract, JP 02304080 A2, Dec. 17, 1990, see entire abstract.

International Search Report for International Application No. PCT/US03/26609 mailed on Apr. 29, 2004.

KETO CANNABINOIDS WITH THERAPEUTIC INDICATIONS

CROSS REFERENCE TO RELATED APPLICATIONS

This application claims the benefit of United States Provisional Application No. 60/405,608, filed Aug. 23, 2002 and U.S. Provisional Application No. 60/405,940, filed Aug. 26, 2002, the contents of each of which are incorporated by reference in their entirety.

STATEMENT REGARDING FEDERALLY SPONSORED RESEARCH OR DEVELOPMENT

This invention was made with U.S. Government support under Contract No. DA3801 and DA7215 awarded by the National Institute of Health. The U.S. Government has certain rights in the invention.

FIELD OF THE INVENTION

This invention relates generally to cannabinoid compounds. One embodiment of the present invention more particularly relates to cannabinoid compounds exhibiting fluorescence properties, particularly in the ultraviolet-visible wavelength ranges.

BACKGROUND OF THE INVENTION

The classical cannabinoid $\Delta^9$-Tetrahydrocannabinol ($\Delta^9$-THC) is the major active constituent extracted from Cannabis sativa. The effects of this, and other, cannabinoids are due to an interaction with specific, high-affinity receptors. Presently, two cannabinoid receptors have been characterized: CB1 and CB2. Characterization of these receptors has been made possible by the development of specific synthetic ligands such as the agonists WIN 55212-2 and CP 55,940.

Additionally, recent scientific discoveries have demonstrated that the endocannabinoid system is very extensive and is currently under intense investigation. Radiochemical methods have been in use for more than a decade for studying the complex phenomena associated with the endocannabinoid system and cannabimimetic molecules. Despite the usefulness and sensitivity of radiochemical methods, the use of alternative methods such as fluorescence techniques can provide information not readily accessible by conventional radiochemical methods and circumvent certain drawbacks associated with them, such as high cost, special precautions in handling and disposal and potential health hazards. Fluorescent approaches provide great advantages over radiochemical methods in accuracy, sensitivity, efficiency, safety and a wide scope of additional applications, and generally are less costly than radiochemical methods. The state-of-art fluorescence approaches enable researchers to detect particular components of complex biomolecular assemblies, including living cells. In particular the emission spectrum of a fluorescer is sensitive to its environment. Therefore, fluorescence approaches are extremely useful in providing spatial, dynamic and temporal information about the interactions between marcomolecules and their ligands.

With the help of available fluorescent ligands, fluorescence techniques have successfully been applied to study the behavior of a number of biological macromolecules, including dopamine receptors, histamine receptors, muscarinic receptors, adrenergic receptors, glucagon receptors, opiate receptors, adenosine receptors and serotonin receptors. The applications of receptor-specific fluorescent ligands are considerably broad, such as molecular studies on ligand-induced conformational changes within the receptor, rapid kinetics of ligand-receptor interactions, the localization of the ligand-binding site on the receptor and distances between different binding sites on the same receptor. Moreover, fluorescent ligands have been successfully used for studying the mobility of some receptors in both normal and pathophysiological conditions by fluorescence photobleach recovery techniques, and to localize receptors at tissue and cellular level by fluorescence microscopic techniques. Furthermore, receptor-specific fluorescent ligands have been employed for receptor assays including the determination of the receptor dissociation constant ($K_D$) and the total receptor content of the tissue ($B_{max}$) by fluorescence titration techniques.

In general, fluorescent ligands are prepared by linking parent ligands with fluorescent moieties to make the newly formed ligands detectable or measurable by fluorescence techniques. Such strategies often face the challenge of reduced potency or efficacy of the parent ligands during interaction with target macromolecules. The inventors are not aware of cannabinoid compounds having fluorescence properties.

SUMMARY OF THE INVENTION

One aspect of the present invention comprises compounds exhibiting fluorescent properties. The fluorescent compounds described in compound formulas I and II are typically endogenously fluorescent and do not rely on linking the cannabinoid compound to a fluorescent moiety. At present, the inventors believe that the compounds described in the compound formulas will have fluorescent properties as long as a long conjugation system (typically comprising the phenyl A ring and a double bond as well as a carbonyl group) can be formed within the tricyclic cannabinoid structure and the Y moiety comprises an electron rich structural element such as nitrogen and oxygen. Some fluorescent cannabinoids not only are capable of generating strong fluorescence, but also can act as high affinity modulators for cannabinoid receptors, and are therefore, of potential usefulness as therapeutic agents through the modulation of the CB1 and/or CB2 cannabinoid receptors.

Another aspect of the present invention comprises compounds exhibiting cannabimimetic activity, both fluorescent and non-fluorescent, pharmaceutical preparations employing these compounds and methods of administering therapeutically effective amounts of these compounds to provide a physiological effect.

Yet another aspect of the invention comprises methods of utilizing the fluorescent compounds.

The novel fluorescent cannabinoid compounds exhibit strong fluorescence, for example in the ultraviolet-visible wavelength ranges. The emission wavelength of some of the inventive compounds ranges from about 390 nm to about 502 nm. The molar extinction constants for some of the inventive compounds ranges from about $1.5 \times 10^4$ to about $2.34 \times 10^4$ (1/Mol×cm/L).

Surprisingly, the cannabinoid compounds in one aspect of the invention, comprising the A, B and C rings of the inventive structure, are intrinsically fluorescent and do not rely on linkage with a fluorescent moiety to achieve their fluorescent properties. Since these inventive fluorescent cannabinoid compounds are intrinsically fluorescent, problems with reduced potency or efficacy are avoided.

In some embodiments the inventive fluorescent cannabinoids not only are capable of generating strong fluorescence, but also can act as high affinity modulators for cannabinoid receptors, and are therefore, of potential usefulness as therapeutic agents through the modulation of the CB1 and/or CB2 cannabinoid receptors.

In general, the compositions of the invention may be alternately formulated to comprise, consist of, or consist essentially of, any appropriate components herein disclosed. The compositions of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

One embodiment of the invention may be represented by compound formula I, and physiologically acceptable salts thereof,

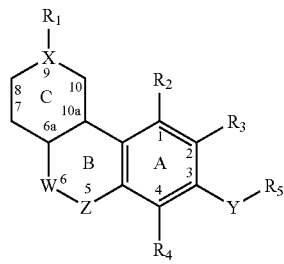

I wherein:
the C ring contains one double bond.

W comprises C=O, C=S or C=CH$_2$. Compound formula I will have advantageous fluorescence properties when W is C=O and the C ring has a double bond in the 6a-10a position. It is believed that compound formula I will have advantageous fluorescence properties when R1 is =O and the C ring has a double bond in the 10-10a position.

X comprises C, CH, N, S, O, SO or SO$_2$.

Y comprises O, S, NH, N-alkyl, N=N, C=C or C≡C.

Z comprises O, NH, N-alkyl where the alkyl group has 1 to about 5 carbon atoms or N-substituted alkyl, where the alkyl group has 1 to about 5 carbon atoms and is substituted with at least one substituent group in any possible position.

When X is S, O, SO or SO$_2$, $R_1$ is not present.

When X is N, $R_1$ comprises H, alkyl, alkoxy-alkyl, alkylmercapto, alkylamino, SO$_3$alkyl, SO$_2$NQ$_1$Q$_2$, CONQ$_1$Q$_2$ or alkyl substituted in any possible position with at least one member selected from OH, CHO, COOH, C(halogen)$_3$, N$_3$, NCS, CN, PO$_3$H$_2$, SO$_3$H, or SO$_3$alkyl.

When X is C or CH, $R_1$ comprises any possible member selected from H, halogen, N$_3$, NCS, CN, NO$_2$, NQ$_1$Q$_2$, =O, OQ$_3$, OAc, O-acyl, O-aroyl, NH-acyl, NH-aroyl, CHO, C(halogen)$_3$, COOQ$_3$, PO$_3$H$_2$, SO$_3$H, SO$_3$alkyl, SO$_2$NQ$_1$Q$_2$, CONQ$_1$Q$_2$, =CH$_2$, alkyl, alcohol, alkoxy, alkylmercapto, alkylamino, di-alkylamino or alkyl substituted in any possible position with at least one substituent group as later defined.

$Q_1$ and $Q_2$ each independently comprise H or alkyl, or
$Q_1$ and $Q_2$ together comprise part of a heterocyclic ring having about 4 to about 7 ring members and optionally one additional heteroatom selected from O, N or S, or
$Q_1$ and $Q_2$ together comprise part of an imide ring having about 5 to about 6 members.

$Q_3$ comprises H, alkyl, hydroxyloweralkyl, or alkyl-NQ$_1$Q$_2$.

In one advantageous variation X is C or CH and $R_1$ comprises any possible member selected from H, halogen, =CH$_2$, an alkyl group having 1 to about 5 carbon atoms or an alkyl group having 1 to about 5 carbon atoms and substituted in any possible position with at least one member selected from OH, CHO, COOH, CH$_2$OH, halogen, C(halogen)$_3$, N$_3$, NCS, CN, PO$_3$H$_2$, SO$_3$H, or SO$_3$alkyl, SO$_2$NQ$_1$Q$_2$, CONQ$_1$Q$_2$, NQ$_1$Q$_2$.

$R_2$ comprises H, OH, OCH$_3$, OPO$_3$H$_2$, OSO$_3$H, PO$_3$H$_2$, SO$_3$H, halogen, NQ$_1$Q$_2$, COOQ$_3$, OQ$_3$, CQ$_3$, C(halogen)$_3$, alkyl-hydroxyl, NH—COalkyl, NH—COaryl, O—COalkyl, O—COalkyl-T$_1$, O—CO-T$_1$, NH—COalkyl-T$_1$, NH—CO-T$_1$, O-alkyl-T$_1$, O-T$_1$, NH-alkyl-T$_1$, NH-T$_1$, SO$_3$alkyl, SO$_2$NQ$_1$Q$_2$.

$T_1$ is in any possible position and comprises PO$_3$H, SO$_3$H, an alkyl group containing from 1 to about 16 carbons, tetrahydropyrrole, morpholine, thiomorpholine, piperazine, a heterocyclic ring or NQ$_1$Q$_2$;

$T_1$ may be substituted in any possible position with at least one member selected from a substituent group, OPO$_3$H$_2$, OSO$_3$H, PO$_3$H$_2$, a heterocyclic ring or a heteroaromatic ring;

$Q_1$ and $Q_2$ each independently comprise H or alkyl, or
$Q_1$ and $Q_2$ together comprise part of a heterocyclic ring having about 4 to about 7 ring members and optionally one additional heteroatom selected from O, N or S, or
$Q_1$ and $Q_2$ together comprise part of an imide ring having about 5 to about 6 members.

$Q_3$ comprises H, alkyl, hydroxyloweralkyl, or alkyl-NQ$_1$Q$_2$.

$R_3$ comprises H, OH, halogen, C(halogen)$_3$, CN, N$_3$, NCS, NQ$_1$Q$_2$ or an alkyl group having 1 to about 4 carbon atoms, $Q_1$ and $Q_2$ each independently comprise H or alkyl, or
$Q_1$ and $Q_2$ together comprise part of a heterocyclic ring having about 4 to about 7 ring members and optionally one additional heteroatom selected from O, N or S, or
$Q_1$ and $Q_2$ together comprise part of an imide ring having about 5 to about 6 members.

$R_4$ comprises H, OH, halogen, CN, N$_3$, NCS, NQ$_1$Q$_2$ or an alkyl group having 1 to about 4 carbon atoms;
$Q_1$ and $Q_2$ each independently comprise H or alkyl, or
$Q_1$ and $Q_2$ together comprise part of a heterocyclic ring having about 4 to about 7 ring members and optionally one additional heteroatom selected from O, N or S, or
$Q_1$ and $Q_2$ together comprise part of an imide ring having about 5 to about 6 members.

$R_5$ comprises -D$_1$-D$_2$-T$_2$ or -D$_2$-T$_2$,

D$_1$, is optionally present and if present, comprises an alkyl group, a carbocyclic ring, a heterocyclic ring, N-alkyl or NH, D$_2$ comprises an alkyl group having from one to about sixteen carbon atoms, a bicyclic ring, a tricyclic ring, a heterocyclic ring, an aromatic ring, a heteroaromatic ring, 1-adamantyl-T$_3$, 2-adamantyl-T$_3$, adamantan-1-ylmethyl-T$_3$ or adamantan-2-ylidenemethyl-T$_3$, alkylamino, di-alkylamino or NH T$_2$ comprises, in any possible position, a substituent group as later defined or —CO-T$_4$, T$_3$ comprises an alkyl group having from 0 to about 9 carbon atoms, T$_4$ comprises H, C-(halogen)$_3$, OH, NH$_2$, alkylamino, di-alkylamino, NO$_2$, alkyl, alkoxy, a heterocyclic ring or a heteroaromatic ring.

In one advantageous variation $R_5$ comprises -D$_1$-D$_2$-T$_2$ or -D$_2$-T$_2$, $D_1$ is optionally present and if present, comprises an alkyl, a carbocyclic ring having 5 to 6 ring members, a heterocyclic ring having 5 to 6 ring members and 1,3 di-heteroatoms each independently selected from O, S, N and NH, $D_2$ comprises an alkyl group having from one to about sixteen carbon atoms, a bicyclic ring, a tricyclic terpine, 1-adamantyl-$T_3$, 2-adamantyl-$T_3$, adamantan-1-ylmethyl-$T_3$ or adamantan-2-ylidenemethyl-$T_3$, alkylamino, di-alkylamino or NH $T_2$ comprises, in any possible position, a substituent group as later defined or —CO-$T_4$, $T_3$ comprises an alkyl group having from 0 to about 9 carbon atoms, $T_4$ comprises alkyl, a heterocyclic ring or a heteroaromatic ring.

Another embodiment of the invention may be represented by compound formula II, and physiologically acceptable salts thereof,

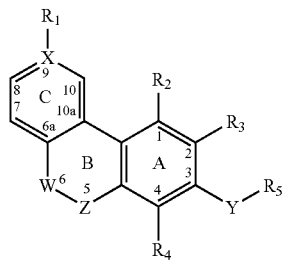

II wherein:

W comprises C=O, C=S, or C=CH$_2$. Advantageously, W comprises C=O. Compound formula II will have advantageous fluorescence properties when W is C=O. It is believed that compound formula II will have advantageous fluorescence properties when R1 is =O.

X comprises C, CH or N.

Y comprises O, S, NH, N-alkyl, N=N, C=C or C≡C.

Z comprises O, NH, N-alkyl where the alkyl group has 1 to about 5 carbon atoms or N-substituted alkyl, where the alkyl group has 1 to about 5 carbon atoms and is substituted with at least one substituent group in any possible position.

$R_1$ comprises any possible member selected from H, halogen, $N_3$, NCS, CN, $NO_2$, $NQ_1Q_2$, $OQ_3$, OAc, O-acyl, O-aroyl, NH-acyl, NH-aroyl, CHO, C(halogen)$_3$, COOQ$_3$, PO$_3$H$_2$, SO$_3$H, SO$_3$alkyl, SO$_2$NQ$_1$Q$_2$, CONQ$_1$Q$_2$, alkyl, alkyl substituted in any possible position with at least one substituent group as later defined.

$Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$Q_3$ comprises H, alkyl, alcohol, or alkyl-NQ$_1$Q$_2$.

In one advantageous variation $R_1$ comprises any possible member selected from H, halogen, OH, an alkyl group having 1 to about 5 carbon atoms or an alkyl group having 1 to about 5 carbon atoms and substituted in any possible position with at least one member selected from OH, CHO, COOH, C(halogen)$_3$, N$_3$, NCS, CN, PO$_3$H$_2$, SO$_3$H, or SO$_3$alkyl.

$R_2$ comprises H, OH, OCH$_3$, OPO$_3$H$_2$, OSO$_3$H, PO$_3$H$_2$, SO$_3$H, halogen, C(halogen)$_3$, alcohol, NQ$_1$Q$_2$, COOQ$_3$, OQ$_3$, alkyl-hydroxyl, NH—COalkyl, NH—COaryl, O—COalkyl, O—COalkyl-$T_1$, O—CO-$T_1$, SO$_2$NQ$_1$Q$_2$, CONQ$_1$Q$_2$, NH—COalkyl-$T_1$, NH—CO-$T_1$, O-alkyl-$T_1$, O-$T_1$, NH-alkyl-$T_1$, NH-TL, SO$_3$alkyl, SO$_2$NQ$_1$Q$_2$.

$T_1$ is in any possible position and comprises PO$_3$H, SO$_3$H, an alkyl group containing from 1 to about 16 carbon atoms, tetrahydropyrrole, morpholine, thiomorpholine, piperazine, a heterocyclic ring or NQ$_1$Q$_2$;

$T_1$ may be substituted in any possible position with at least one member selected from a substituent group, OPO$_3$H$_2$, OSO$_3$H, PO$_3$H$_2$, a heterocyclic ring or a heteroaromatic ring;

$Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$Q_3$ comprises H, alkyl, alcohol, or alkyl-NQ$_1$Q$_2$.

$R_3$ comprises H, OH, halogen, C(halogen)$_3$, CN, N$_3$, NCS, NQ$_1$Q$_2$ or C1 to C$_4$ alkyl, $Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$R_4$ comprises H, OH, halogen, C(halogen)$_3$, CN, N$_3$, NCS, NQ$_1$Q$_2$ or C1 to C4 alkyl;

$Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$R_5$ comprises -$D_1$-$D_2$-$T_2$ or -$D_2$-$T_2$, $D_1$ is optionally present and if present, comprises an alkyl, a carbocyclic ring, a heterocyclic ring, alkylamino or NH, $D_2$ comprises an alkyl group having from one to about sixteen carbon atoms, a bicyclic ring, a tricyclic ring, a heterocyclic ring, an aromatic ring, a heteroaromatic ring, 1-adamantyl-$T_3$, 2-adamantyl-$T_3$, adamantan-1-ylmethyl-$T_3$, or adamantan-2-ylidenemethyl-$T_3$, alkylamino, di-alkylamino or NH, $T_2$ comprises, in any possible position, a substituent group as later defined or —CO-$T_4$, $T_3$ comprises an alkyl group having from 0 to about 9 carbon atoms, $T_4$ comprises H, C(halogen)$_3$, OH, NH$_2$, NO$_2$, alkyl, alkoxy, a heterocyclic ring or a heteroaromatic ring.

In one advantageous variation $R_5$ comprises -$D_1$-$D_2$-$T_2$ or -$D_2$-$T_2$ $D_1$ comprises alkylamino, di-alkylamino, NH, a carbocyclic ring having 4 to 6 ring members or a heterocyclic ring having 4 to 6 ring members and 1,3 di-heteroatoms each heteroatom independently selected from O, S and N, $D_2$ comprises an alkyl group having from one to about sixteen carbon atoms, a bicyclic ring, a tricyclic terpine, 1-adamantyl-$T_3$, 2-adamantyl-$T_3$, adamantan-1-ylmethyl-$T_3$ or adamantan-2-ylidenemethyl-$T_3$, alkylamino, di-alkylamino or NH $T_2$ comprises, in any possible position, a substituent group as later defined or —CO-$T_4$, $T_3$ comprises an alkyl group having from 0 to about 9 carbon atoms, $T_4$ comprises alkyl, a heterocyclic ring or a heteroaromatic ring.

Another embodiment of the invention may be represented by either compound formula 1 or II, wherein:

The C ring in compound formula I contains a double bond in the 6a-10a position.

W is C=O.

X comprises C or N.

Y comprises O, S, NH, N-alkyl, N=N, C=C, C≡C,

Z is O.

$R_1$ comprises OH, $CH_2OH$, in compound formula I; or methyl, OH, $CH_2OH$ in compound formula II.

$R_2$ comprises H, OH, $OCH_3$, $OPO_3H_2$, $OSO_3H$, $PO_3H_2$, $SO_3H$, halogen, $C(halogen)_3$, alcohol, $NQ_1Q_2$, $COOQ_3$, $OQ_3$, NH—COalkyl, NH—CO-aryl, O—COalkyl, O—COalkyl-$T_1$, O—CO-$T_1$, NH—COalkyl-$T_1$, NH—CO-$T_1$, O-alkyl-$T_1$, O-$T_1$, NH-alkyl-$T_1$, NH-$T_1$, $SO_3$alkyl, $SO_2NQ_1Q_2$ or $CONQ_1Q_2$ $T_1$ is in any possible position and comprises $PO_3H$, $SO_3H$, an alkyl group containing from 1 to about 16 carbon atoms, tetrahydropyrrole, morpholine, thiomorpholine, piperazine, a heterocyclic ring or $NQ_1Q_2$;

$T_1$ may be substituted in any possible position with at least one member selected from a substituent group, $OPO_3H_2$, $OSO_3H$, $PO_3H_2$, a heterocyclic ring or a heteroaromatic ring;

$Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$Q_3$ comprises H, alkyl, hydroxyloweralkyl, or alkyl-$NQ_1Q_2$.

$R_3$ comprises H, OH, halogen, $C(halogen)_3$, CN, $N_3$, NCS, $NQ_1Q_2$ or an alkyl group having 1 to about 4 carbon atoms, $Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$R_4$ comprises H, OH, halogen, $C(halogen)_3$, CN, $N_3$, NCS, $NQ_1Q_2$ or an alkyl group having 1 to about 4 carbon atoms;

$Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$R_5$ comprises -$D_1$-$D_2$-$T_2$ or -$D_2$-$T_2$, $D_1$ is optionally present and if present, comprises an alkyl, a carbocyclic ring, a heterocyclic ring, alkylamino or NH.

$D_2$ comprises an alkyl group having from one to about sixteen carbon atoms, a bicyclic ring, a tricyclic ring, 1-adamantyl-$T_3$, 2-adamantyl-$T_3$, adamantan-1-ylmethyl-$T_3$, or adamantan-2-ylidenemethyl-$T_3$, alkylamino, di-alkylamino or NH.

$T_2$ comprises, in any possible position, a substituent group as later defined or —CO-$T_4$, $T_3$ comprises an alkyl group having from 0 to about 9 carbon atoms, $T_4$ comprises H, $C(halogen)_3$, OH, $NH_2$, $NO_2$, alkyl, alkoxy, alkylamino, di-alkylamino, a heterocyclic ring or a heteroaromatic ring.

In one advantageous variation $R_5$ comprises -$D_1$-$D_2$-$T_2$ or -$D_2$-$T_2$, $D_1$ is optionally present and if present, comprises an alkyl, a carbocyclic ring having 4 to 6 ring members or a heterocyclic ring having 4 to 6 ring members and 1,3 di-heteroatoms each heteroatom independently selected from O, S and N.

$D_2$ comprises an alkyl group having from one to about sixteen carbon atoms, alkylamino, d-alkylamino, NH, a bicyclic ring, a tricyclic ring, 1-adamantyl-$T_3$, 2-adamantyl-$T_3$, adamantan-1-ylmethyl-$T_3$ or adamantan-2-ylidenemethyl-$T_3$.

$T_2$ comprises, in any possible position, a substituent group as later defined or —CO-$T_4$, $T_3$ comprises an alkyl group having from 0 to about 9 carbon atoms, $T_4$ comprises alkyl, $C(halogen)_3$ aminoalkyl, di-aminoalkyl, NH2, a heterocyclic ring or a heteroaromatic ring.

Another embodiment of the invention comprises compound formula II, and physiologically acceptable salts thereof,

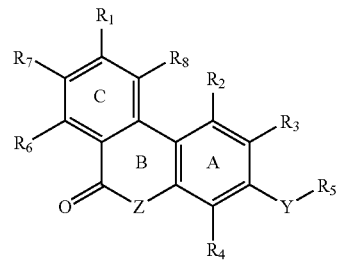

wherein:

Y comprises $CH_2$, $CH(CH_3)$, $C(CH_3)_2$, a carbocyclic ring having 4 to 6 ring members or a heterocyclic ring having 4 to 6 ring members with 1 or 2 heteroatoms.

Z comprises O, S, NH, N-alkyl where alkyl comprises 1 to about 5 carbon atoms.

$R_1$ comprises H, halogen, $N_3$, NCS, CN, $NO_2$, $NQ_1Q_2$, =O, $OQ_3$, OAc, O-acyl, O-aroyl, NH-acyl, NH-aroyl, CHO, $C(halogen)_3$, $COOQ_3$, $PO_3H_2$, $SO_3H$, $SO_3$alkyl, $SO_2NQ_1Q_2$, $CONQ_1Q_2$, =$CH_2$, alkyl, alcohol, alkoxy, alkylmercapto, alkylamino, di-alkylamino or alkyl substituted in any possible position with at least one member selected from the substituent groups defined later.

$R_2$ comprises H, OH, $OCH_3$, $OPO_3H_2$, $OSO_3H$, $PO_3H_2$, $SO_3H$, halogen, C-$(halogen)_3$, $NQ_1Q_2$, $COOQ_3$, $OQ_3$, NH—COalkyl, NH—COaryl, O—COalkyl, O—COalkyl-$T_1$, O—CO-$T_1$, alkyl-hydroxyl, NH—COalkyl-$T_1$, NH—CO-$T_1$, O-alkyl-$T_1$, O-$T_1$, NH-alkyl-$T_1$, NH-$T_1$, $SO_3$alkyl, $SO_2NQ_1Q_2$ or $CONQ_1Q_2$ $T_1$ is in any possible position and comprises $PO_3H$, $SO_3H$, an alkyl group containing from 1 to about 16 carbons, tetrahydropyrrole, morpholine, thiomorpholine, piperazine, a heterocyclic ring or $NQ_1Q_2$;

$T_1$ may be substituted in any possible position with at least one member selected from a substituent group, $OPO_3H_2$, $OSO_3H$, $PO_3H_2$, a heterocyclic ring or a heteroaromatic ring;

$Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$Q_3$ comprises H, alkyl, alcohol or alkyl-$NQ_1Q_2$.

$R_3$, $R_4$, $R_6$, $R_7$, or $R_8$ each independently comprise H, OH, halogen, C(halogen)$_3$, CN, $N_3$, NCS, $NQ_1Q_2$ or an alkyl group having 1 to about 4 carbon atoms, $Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$R_5$ comprises -$D_1$-$D_2$-$T_2$ or -$D_2$-$T_2$, with the below listed provisos.

$D_1$ is optionally present and if present, comprises an alkyl, a carbocyclic ring, a heterocyclic ring.

$D_2$ comprises an alkyl group having from one to about sixteen carbon atoms, alkylamino, di-alkylamino, NH, a bicyclic ring, a tricyclic ring, 1-adamantyl-$T_3$, 2-adamantyl-$T_3$, adamantan-1-ylmethyl-$T_3$, or adamantan-2-ylidenemethyl-$T_3$, $T_2$ comprises, in any possible position, a substituent group as later defined, —CO-$T_4$, a heterocyclic ring, a heterobicyclic ring structure, a heterotricyclic ring structure, a heteropolycyclic ring structure or a heteroaromatic ring with or without a substituent group as later defined.

$T_3$ comprises an alkyl group having from 0 to about 9 carbon atoms, $T_4$ comprises H, C(halogen)$_3$, OH, $NH_2$, $NO_2$, alkyl, alkoxy, a heterocyclic ring or a heteroaromatic ring.

Provisos with respect to Structure Formula III:

When $R_3$, $R_4$, $R_6$, $R_7$ and $R_8$ are each H; $R_1$ is methyl; and $R_2$ is OH, then Y—$R_5$ can not be C(CH$_3$)$_2$(CH2)$_5$CH$_3$, CH(CH$_2$CH$_3$)$_2$ or CH2(CH$_2$)$_3$CH$_3$.

When $R_3$, $R_4$, $R_6$, $R_7$ and $R_8$ are each H; $R_1$ is methyl; and Y—$R_5$ is n-pentyl, then $R_2$ can not be OCOCH$_3$, OCH(CH$_3$)COCH$_3$, OCH$_2$CH(OC$_2$H$_5$)$_2$ or OCH$_2$CHO.

When $R_3$, $R_4$, $R_6$, $R_7$ and $R_8$ are each H; $R_1$ is bromide; and $R_2$ is OH, then Y—$R_5$ can not be n-pentyl.

When $R_1$ is CH$_3$; $R_2$ is OH; and one of $R_7$ and $R_8$ is OH and the other is H, Y—$R_5$ can not be n-pentyl.

When $R_3$, $R_4$, $R_6$, $R_7$ and $R_8$ are each H; formula III excludes compounds constructed by the combination of selecting $R_1$ from any of OH; OCH$_3$, OC$_2$H$_5$, OC$_3$H$_7$, OC$_4$H$_9$, and selecting Y—$R_5$ from any of (CH$_2$)$_q$CH$_3$, C(CH$_3$)$_2$(CH$_2$)$_q$CH$_3$; (CH$_2$)$_q$—C≡C; C≡C(CH$_2$)$_q$; alkyl substituted adamantyl, as well as selecting Y from any five member ring and $R_5$ from (CH$_2$)$_q$CH$_3$, wherein q is an integer from 3-6.

In one advantageous variation, $R_1$ comprises halogen, C(halogen)$_3$, CH$_2$OH, a substituent group as later defined, an alkyl group having 1 to about 5 carbon atoms or an alkyl group having 1 to about 5 carbon atoms and substituted in any possible position with at least one member selected from substituent groups defined later.

$R_2$ comprises H, OH, OCH$_3$, OPO$_3$H$_2$, OSO$_3$H, PO$_3$H$_2$, SO$_3$H, halogen, C(halogen)$_3$, $NQ_1Q_2$, alkyl-hydroxyl, COOQ$_3$, OQ$_3$, NH—COalkyl, NH—COaryl, O—COalkyl, O—COalkyl-$T_1$, O—CO-$T_1$, NH—COalkyl-$T_1$, NH—CO-$T_1$, O-alkyl-$T_1$, O-$T_1$, NH-alkyl-$T_1$, NH-$T_1$, SO$_3$alkyl, SO$_2$NQ$_1$Q$_2$ or CONQ$_1$Q$_2$.

$T_1$ is in any possible position and comprises PO$_3$H, SO$_3$H, an alkyl group containing from 1 to about 16 carbons, tetrahydropyrrole, morpholine, thiomorpholine, piperazine, a heterocyclic ring or NQ$_1$Q$_2$;

$T_1$ may be substituted in any possible position with at least one member selected from a substituent group, OPO$_3$H$_2$, OSO$_3$H, PO$_3$H$_2$, a heterocyclic ring or a heteroaromatic ring;

$Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$Q_3$ comprises H, alkyl, alcohol, or alkyl-NQ$_1$Q$_2$.

$R_3$, $R_4$, $R_6$, $R_7$ and $R_8$ comprises H, OH, halogen, C(halogen)$_3$, CN, $N_3$, NCS, NQ$_1$Q$_2$ or an alkyl group having 1 to about 4 carbon atoms, $Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$R_5$ comprises -$D_1$-$D_2$-$T_2$ or -$D_2$-$T_2$, $D_1$ is optionally present and if present, comprises an alkyl group, a carbocyclic ring or a heterocyclic ring, $D_2$ comprises an alkyl group having from one to about sixteen carbon atoms, alkylamino, di-alkylamino, NH, a bicyclic ring, a tricyclic ring, 1-adamantyl-$T_3$, 2-adamantyl-$T_3$, adamantan-1-ylmethyl-$T_3$ or adamantan-2-ylidenemethyl-$T_3$, $T_2$ comprises, in any possible position, a substituent group as later defined or —CO-$T_4$, $T_3$ comprises an alkyl group having from 0 to about 9 carbon atoms, $T_4$ comprises H, C(halogen)$_3$, OH, NH$_2$, alkylamino, di-alkylamino, NO$_2$, alkyl, alkoxy, a heterocyclic ring or a heteroaromatic ring.

Another embodiment of the invention comprises compound formula IV, and physiologically acceptable salts thereof,

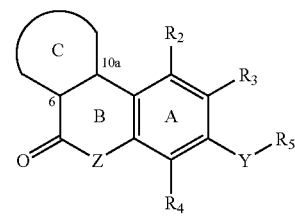

IV wherein:

The "C" Ring of compound formula IV comprises a carbocyclic ring, a bicyclic ring structure, a tricyclic ring structure, a heterocyclic ring, a heterobicyclic ring structure, or a heteroaromatic ring.

Y comprises CH$_2$, CHCH$_3$, C(CH$_3$)$_2$, a carbocyclic ring, an aromatic ring, a heterocyclic ring or a heteroaromatic ring, Z comprises O, S, NH or N-alkyl.

$R_2$ comprises H, OH, OCH$_3$, OPO$_3$H$_2$, OSO$_3$H, PO$_3$H$_2$, SO$_3$H, halogen, C-(halogen)$_3$, alkyl-hydroxyl, NQ$_1$Q$_2$, COOQ$_3$, OQ$_3$, NH—COalkyl, NH—COaryl, O—COalkyl, O—COalkyl-$T_1$, O—CO-$T_1$, NH—COalkyl-$T_1$, NH—CO-$T_1$, O-alkyl-$T_1$, O-$T_1$, NH-alkyl-$T_1$, NH-$T_1$, $SO_3$alkyl, $SO_2NQ_1Q_2$ or $CONQ_1Q_2$.

$T_1$ is in any possible position and comprises $PO_3H$, $SO_3H$, an alkyl group containing from 1 to about 16 carbons, tetrahydropyrrole, morpholine, thiomorpholine, piperazine, a heterocyclic ring or $NQ_1Q_2$;

$T_1$ may be substituted in any possible position with at least one member selected from a substituent group, $OPO_3H_2$, $OSO_3H$, $PO_3H_2$, a heterocyclic ring or a heteroaromatic ring;

$Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$Q_3$ comprises H, alkyl, alcohol, or alkyl-$NQ_1Q_2$.

$R_3$ and $R_4$ each independently comprise H, OH, halogen, C-(halogen)$_3$, CN, $N_3$, NCS, $NQ_1Q_2$ or an alkyl group having 1 to about 4 carbon atoms, $Q_1$ and $Q_2$ each independently comprise H or alkyl, or $Q_1$ and $Q_2$ together comprise part of a heterocyclic ring having about 4 to about 7 ring members and optionally one additional heteroatom selected from O, N or S, or $Q_1$ and $Q_2$ together comprise part of an imide ring having about 5 to about 6 members.

$R_5$ comprises -$D_1$-$D_2$-$T_2$ or -$D_2$-$T_2$, with the below listed provisos.

$D_1$ is optionally present and if present, comprises an alkyl, a carbocyclic ring or a heterocyclic ring.

$D_2$ comprises an alkyl group having from one to about sixteen carbon atoms, alkylamino, di-alkylamino, NH, a bicyclic ring, a tricyclic ring, 1-adamantyl-$T_3$, 2-adamantyl-$T_3$, adamantan-1-ylmethyl-$T_3$, or adamantan-2-ylidenemethyl-$T_3$.

$T_2$ comprises, in any possible position, a substituent group as later defined, —CO-$T_4$, a heterocyclic ring, a heterobicyclic ring structure, a heterotricyclic ring structure, a heteropolycyclic ring structure or a heteroaromatic ring with or without a substituent group as later defined.

$T_3$ comprises an alkyl group having from 0 to about 9 carbon atoms, $T_4$ comprises H, halogen, OH, $NH_2$, $NO_2$, alkyl, alkoxy, a heterocyclic ring or a heteroaromatic ring, with the proviso that when the C ring is 4-methyl cyclohexane with a double bond between the 6 and 10a positions, then Y—$R_5$ can not be a saturated alkyl group.

Provisos with respect to Structure Formula IV:

When the C ring is a pyridine or N-methyl-pyridine structure having the nitrogen in the para position to the carbonyl of B ring; $R_3$ and $R_4$ are hydrogen; then Y—$R_5$ can not be a straight or branched alkyl chain of 1 to 20 carbon atoms.

When the C ring is 4-methyl hexane having the methyl in the para position to the carbonyl of B ring; $R_3$ and $R_4$ are hydrogen; then Y—$R_5$ can not be $CH_2COOH$ or a straight or branched chain alkyl of 1 to 20 carbon atoms.

When the C ring is a N-methyl tetrahydropridine having a nitrogen in the para position to the carbonyl of the B ring; $R_3$ and $R_4$ are hydrogen; $R_2$ is OH; then Y—$R_5$ can not be OH, N—$C_5H_1$, $CH(CH_3)(CH_2)_4CH_3$, $(CH2)11CH_3$, or CH(cyclohexanyl).

When the C ring is a tetrahydroprydine having a nitrogen in the para position to the carbonyl of the B ring; $R_3$ and $R_4$ are hydrogen; Y—$R_5$ is 1.2-dimethylhexanyl; $R_2$ is OH; then the nitrogen of C ring can not be substituted with H, $CHC_6H_6$, $CH_3$ or $CH_2C\equiv CH$.

When the C ring is a N-benzyl-tetrahydropridine having a nitrogen in the para position to the carbonyl of the B ring; $R_3$ and $R_4$ are hydrogen; $R_2$ is OH; then Y—$R_5$ can not be $CH(CH_3)CH_2COOCH_3$, $CH(CH_3)CH_2COOH$, $CH(CH_3)CH_2COCH_3$, $CH(CH_3)CH_2COOH$ $CH_2CH_3$ or $CH(CH_3)CH_2C(CH_3)_2OH$.

Unless otherwise specifically defined, "acyl" refers to the general formula —C(O)alkyl.

Unless otherwise specifically defined, "acyloxy" refers to the general formula —O-acyl.

Unless otherwise specifically defined, "alcohol" refers to the general formula alkyl-OH and includes primary, secondary and tertiary variations.

Unless otherwise specifically defined, "alkyl" or "lower alkyl" refers to a linear, branched or cyclic alkyl group having from 1 to about 16 carbon atoms including, for example, methyl, ethyl, propyl, butyl, hexyl, octyl, isopropyl, isobutyl, tert-butyl, cyclopropyl, cyclohexyl, cyclooctyl, vinyl and allyl. The alkyl group can be saturated or unsaturated. Unless otherwise specifically limited, an alkyl group can be unsubstituted, singly substituted or, if possible, multiply substituted, with substituent groups in any possible position. Unless otherwise specifically limited, a cyclic alkyl group includes monocyclic, bicyclic, tricyclic and polycyclic rings, for example norbornyl, adamantyl and related terpenes.

Unless otherwise specifically defined, "alkoxy" refers to the general formula —O-alkyl.

Unless otherwise specifically defined, "alkylmercapto" refers to the general formula —S-alkyl.

Unless otherwise specifically defined, "alkylamino" refers to the general formula —(NH)-alkyl.

Unless otherwise specifically defined, "di-alkylamino" refers to the general formula —N(alkyl)$_2$. Unless otherwise specifically limited di-alkylamino includes cyclic amine compounds such as piperidine and morpholine.

Unless otherwise specifically defined, an aromatic ring is an unsaturated ring structure having about 5 to about 7 ring members and including only carbon as ring atoms. The aromatic ring structure can be unsubstituted, singly substituted or, if possible, multiply substituted, with substituent groups in any possible position.

Unless otherwise specifically defined, "aryl" refers to an aromatic ring system that includes only carbon as ring atoms, for example phenyl, biphenyl or naphthyl. The aryl group can be unsubstituted, singly substituted or, if possible, multiply substituted, with substituent groups in any possible position.

Unless otherwise specifically defined, "aroyl" refers to the general formula —C(=O)-aryl.

Unless otherwise specifically defined, a bicyclic ring structure comprises 2 fused or bridged rings that include only carbon as ring atoms. The bicyclic ring structure can be saturated or unsaturated. The bicyclic ring structure can be unsubstituted, singly substituted or, if possible, multiply substituted, with substituent groups in any possible position. The individual rings may or may not be of the same type. Examples of bicyclic ring structures include, Dimethyl-bicyclo[3,1,1]heptane, bicyclo[2,2,1]heptadiene, decahydro-naphthalene and bicyclooctane.

Unless otherwise specifically defined, a carbocyclic ring is a non-aromatic ring structure, saturated or unsaturated, having about 3 to about 8 ring members that includes only carbon as ring atoms, for example, cyclohexadiene or cyclohexane. The carbocyclic ring can be unsubstituted, singly substituted or, if possible, multiply substituted, with substituent groups in any possible position.

Unless otherwise specifically defined, "fluorescence" refers to the emission of, or the property of emitting, electromagnetic radiation by a molecule resulting from and occurring only when that molecule is excited by the absorption of radiation from some other source.

Unless otherwise specifically defined, "halogen" refers to an atom selected from fluorine, chlorine, bromine and iodine.

Unless otherwise specifically defined, a heteroaromatic ring is an unsaturated ring structure having about 5 to about 8 ring members that has carbon atoms and one or more heteroatoms, including oxygen, nitrogen and/or sulfur, as ring atoms, for example, pyridine, furan, quinoline, and their derivatives. The heteroaromatic ring can be unsubstituted, singly substituted or, if possible, multiply substituted, with substituent groups in any possible position.

Unless otherwise specifically defined, a heterobicyclic ring structure comprises 2 fused or bridged rings that include carbon and one or more heteroatoms, including oxygen, nitrogen and/or sulfur, as ring atoms. The heterobicyclic ring structure is saturated or unsaturated. The heterobicyclic ring can be unsubstituted, singly substituted or, if possible, multiply substituted, with substituent groups in any possible position. The individual rings may or may not be of the same type.

Examples of heterobicyclic ring structures include tropane, quinuclidine and tetrahydro-benzofuran.

Unless otherwise specifically defined, a heterocyclic ring is a saturated or unsaturated ring structure having about 3 to about 8 ring members that has carbon atoms and one or more heteroatoms, including oxygen, nitrogen and/or sulfur, as ring atoms, for example, piperidine, morpholine, piperazine, pyrrolidine, thiomorpholine, tetrahydropyridine, and their derivatives. The heterocyclic ring can be unsubstituted, singly substituted or, if possible, multiply substituted, with substituent groups in any possible position.

Unless otherwise specifically defined, a heterotricyclic ring structure comprises 3 rings that may be fused, bridged or both fused and bridged, and that include carbon and one or more heteroatoms, including oxygen, nitrogen and/or sulfur, as ring atoms. The heterotricyclic ring structure can be saturated or unsaturated. The heterotricyclic ring structure can be unsubstituted, singly substituted or, if possible, multiply substituted, with substituent groups in any possible position. The individual rings may or may not be of the same type. Examples of heterotricyclic ring structures include 2,4,10-trioxaadamantane, tetradecahydro-phenanthroline.

Unless otherwise specifically defined, a heteropolycyclic ring structure comprises more than 3 rings that may be fused, bridged or both fused and that include carbon and one or more heteroatoms, including oxygen, nitrogen and/or sulfur, as ring atoms. The heteropolycyclic ring structure can be saturated or unsaturated. The heteropolycyclic ring structure can be unsubstituted, singly substituted or, if possible, multiply substituted, with substituent groups in any possible position. The individual rings may or may not be of the same type. Examples of heteropolycyclic ring structures include azaadamantine, 5-norbornene-2,3-dicarboximide.

Unless otherwise specifically defined, the term "phenacyl" refers to the general formula -phenyl-acyl.

Unless otherwise specifically defined, a polycyclic ring structure comprises more than 3 rings that may be fused, bridged or both fused and bridged, and that includes carbon as ring atoms. The polycyclic ring structure can be saturated or unsaturated. The polycyclic ring structure can be unsubstituted, singly substituted or, if possible, multiply substituted, with substituent groups in any possible position. The individual rings may or may not be of the same type. Examples of polycyclic ring structures include adamantine, bicyclooctane, norbornane and bicyclononanes.

Unless otherwise specifically defined, a spirocycle refers to a ring system wherein a single atom is the only common member of two rings. A spirocycle can comprise a saturated carbocyclic ring comprising about 3 to about 8 ring members, a heterocyclic ring comprising about 3 to about 8 ring atoms wherein up to about 3 ring atoms may be N, S, or O or a combination thereof.

Unless otherwise specifically defined, a tricyclic ring structure comprises 3 rings that may be fused, bridged or both fused and bridged, and that includes carbon as ring atoms. The tricyclic ring structure can be saturated or unsaturated. The tricyclic ring structure can be unsubstituted, singly substituted or, if possible, multiply substituted, with substituent groups in any possible position. and may be substituted or unsubstituted. The individual rings may or may not be of the same type. Examples of tricyclic ring structures include fluorene and anthracene.

Unless otherwise specifically limited the term substituted means substituted by a below described substituent group in any possible position. Substituent groups for the above moieties useful in the invention are those groups that do not significantly diminish the biological activity of the inventive compound. Unless otherwise specifically limited a substituent group or a substituent group that does not significantly diminish the biological activity of the inventive compound includes, for example, H, halogen, $N_3$, NCS, CN, $NO_2$, $NX_1X_2$, $OX_3$, $C(X_3)_3$, OAc, O-acyl, O-aroyl, NH-acyl, NH-aroyl, NHCOalkyl, CHO, C(halogen)$_3$, $COOX_3$, $SO_3H$, $PO_3H_2$, $SO_2NX_1X_2$, $CONX_1X_2$, alkyl, alcohol, alkoxy, alkylmercapto, alkylamino, di-alkylamino, sulfonamide or thioalkoxy wherein $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members and $X_3$ comprises H, alkyl, loweralkylhydroxy, or alkyl-$NX_1X_2$. Unless otherwise specifically limited, a substituent group may be in any possible position.

Some of the inventive cannabinoid compounds exhibit high affinity for the CB1 and/or CB2 cannabinoid receptors. Thus, another aspect of the invention is use of at least one of the inventive compounds to interact with cannabinoid receptors.

Further, some of the inventive cannabinoid compounds show a surprisingly higher selectivity for one of the cannabinoid receptors. These inventive selective compounds are able to interact with one cannabinoid receptor, for example the CB2 cannabinoid receptor, without affecting the other cannabinoid receptor to the same degree. Therefore, still another aspect of the invention is use of at least one of the inventive compounds to preferentially interact with one cannabinoid receptor.

Some of the inventive compounds exhibit fluorescence properties. Therefore, still another aspect of the invention is the use of the fluorescent properties of cannabinoid compounds. In a variation, the fluorescence properties allow qualitative or quantitative detection of the cannabinoid compounds and or their complex with cannabinoid receptors.

Some of the inventive fluorescent cannabinoid compounds exhibit high affinity and/or selectivity for the CB1 and/or CB2 cannabinoid receptors. Therefore, still another aspect of the invention is a method of using the inventive fluorescent cannabinoid compounds as fluorescent biosensors. In some embodiments the inventive method is capable of sensing and reporting the bio-behaviors of cannabinoid receptors and molecules associated with the cannabinoid receptors through a variety of fluorescence technologies.

Some applicable fluorescence technologies useful with the inventive method include, for example, Fluorescence Microscopy, Fluorescence Polarization Spectroscopy, Fluorescence Resonance Energy Transfer Analysis, Flow Cytometry, Fluorescence Photo-Bleach, Immunofluorescence, and Fluorescent Competitive Binding Assay. It should be understood that the present method encompasses use of the inventive compounds in any technology wherein their fluorescent properties are desirable. Thus, the inventive fluorescent cannabinoids can be employed as Fluorescent Molecular Probes, Fluorescent Imaging Agents, Fluorescent Control Standards and Cellular Markers in a broad scope of biomedical research involving cannabinoid receptors. In addition, the fluorescent cannabinoids can be applied in clinical use as Fluorescent Diagnostic Agents to determine therapeutic drug levels and the presence of drugs of abuse in fluids. The fluorescent cannabinoids can also be used as diagnostic agents for determination of white blood cells that have a high concentration of CB2 receptors.

Some of the inventive cannabinoid compounds can act as high affinity modulators for cannabinoid receptors. The inventive cannabinoid compounds therefore are potential therapeutic agents through the modulation of the CB1 and/or CB2 cannabinoid receptors.

Some of the novel cannabinoid compounds described herein may be cannabinoid receptor agonists. The inventive cannabinoid agonists interact with the CB1 and/or CB2 cannabinoid receptor binding site to initiate a physiological or a pharmacological response characteristic of that receptor. Therefore, a further aspect of the invention is use of at least one of the inventive compounds to initiate an agonistic response from a cannabinoid receptor.

Some of the novel cannabinoid compounds described herein may be cannabinoid receptor antagonists. The inventive cannabinoid antagonists interact with the CB1 and/or CB2 cannabinoid receptor binding site to block other ligands from the receptor binding site without initiating a physiological or a pharmacological response characteristic of that receptor. Thus, cannabinoid antagonists typically oppose the cannabinoid receptor site response characteristics initiated by cannabinoid agonists. Therefore, a further aspect of the invention is use of at least one of the inventive compounds to oppose initiation of an agonistic response from a cannabinoid receptor.

The inventive cannabinoid compounds described herein, and physiologically acceptable salts thereof, have pharmacological properties when administered in therapeutically effective amounts for providing a physiological response in individuals and/or animals. Thus, another aspect of the invention is the administration of a therapeutically effective amount of at least one of the inventive compounds, or a physiologically acceptable salt thereof, to an individual or animal to provide a physiological response.

A better understanding of the invention will be obtained from the following detailed description of the article and the desired features, properties, characteristics, and the relation of the elements as well as the process steps, one with respect to each of the others, as set forth and exemplified in the description and illustrative embodiments.

DESCRIPTION OF SOME PREFERRED EMBODIMENTS

The use of radiolabeled cannabinoid compounds in research (for example in binding assays) is well known, as are the problems with obtaining, using and disposal of radioactive compounds. The inventive fluorescent cannabinoid compounds can be used to conduct research in a similar manner as radiolabeled compounds. However, fluorescent techniques such as, for example, Fluorescence Resonance Energy Transfer (FRET) can be used to assess results of the research in place of radiocounting techniques. Naturally, the inventive compounds provide benefits in procurement, handling and disposal over radioactive compounds. Additionally, fluorescence techniques are highly specific and sensitive, so that the inventive compounds can provide improvements in specificity and sensitivity over radiotechniques.

Fluorescent ligands are generally useful to probe and sense receptor mechanism include the histochemical localization of receptors, their visualization on cell surface, quantification of receptor mobility by the technique of fluorescence recovery after photobleaching, and fluorescent energy transfer experiments to characterize the receptor environment, e.g. the lipid bilayer in membrane or the topolography of binding sites on isolated receptor molecules.

The potential applications of the inventive fluorescent cannabinoids as biosensor, molecular probe, cellular marker and imaging agent can be extrapolated from numerous published works employing fluorescent ligands in other, non-cannabinoid biological system. For instance, Ariano M. A. et al described the visualization of dopamine receptors by using fluorescent ligands as imaging agents (*Multiple fluorescent ligands for dopamine receptors. II. Visualization in neural tissues*. Brain Res. 1991 May 3;547(2):208–22), Melamed E. reported the visualization of beta-adrenoceptor in rat cerebellum via a fluorescent analogue of propranolol (*Direct localisation of beta-adrenoceptor sites in rat cerebellum by a new fluorescent analogue of propranolol*, Nature. 1976 Jun. 3;261(5559):420–2), and Miksicek R J et al described the imaging of estrogen receptors by a fluorescent ligand (*In situ localization of the estrogen receptor in living cells with the fluorescent phytoestrogen coumestrol*. J Histochem Cytochem. 1993 June;41(6):801–10). Furthermore, applications of fluorescent compounds as molecular probes or biosensors can be exemplified by the work of McCabe R T (*Characterization of benzodiazepine receptors with fluorescent ligands*, FASEB J. 1990 Aug.; 4(11):2934–40); Vallotton P, (*Mapping The Antagonist Binding Site of The Serotonin Type 3 Receptor by Fluorescence Resonance Energy Transfer*, Biochemistry, 2001 Oct. 16;40(41):12237–42); Jones G, (*Azole-linked coumarin dyes as fluorescence probes of domain-forming polymers*, J Photochem Photobiol B. 2001 Dec. 1;65(1):5–12); Vallotton P et al (*In Vitro and In Vivo Ligand Binding to the 5HT(3) Serotonin Receptor Characterised by Time-Resolved Fluorescence Spectroscopy*, Chembiochem Europ J Chem Biol. 2001 Mar. 2;2(3):205–11), Epand R F, (*Fluorescent probes of membrane surface properties, Biochim Biophys Acta*, 1996 Oct. 23;1284(2):191–5); Balice-Gordon R J (*In vivo observations of pre- and postsynaptic changes during the transition from multiple to single innervation at developing neuromuscular junctions*, J. Neurosci. 1993 Feb.; 13(2): 834–55) Yamamoto T (*Spectroscopic monitoring of local conformational chances during the intramolecular domain-domain interaction of the ryanodine receptor*, Biochemistry. 2002 Feb. 5;41(5):1492–501); Janssen M J et al (*A fluorescent receptor assay for benzodiazepines using coumarin-labeled desethylflumazenil as ligand*. Anal Chem. 2001 Jul.1;73(13):3168–73), Guatimosim C et al (*Use of fluorescent probes to follow membrane traffic in nerve terminals*. Braz J Med Biol Res. 1998 Nov.; 31(11):1491–500), and Hazum E (*Cluster formation of opiate (enkephalin) receptors in neuroblastoma cells: differences between agonists and antagonists and possible relationships to biological functions*, Proc Natl Acad Sci USA. 1980 May;77(5): 3038–41).

Some fluorescent compounds have also been used as diagnostic agents. For example, Cortvrindt R G et al described a method of using a non-cannabinoid fluorescent compound to detect follicle density and staging in human ovarian cortical biopsy samples (*Fluorescent probes allow rapid and precise recording of follicle density and staging in human ovarian cortical biopsy samples*. Fertil Steril. 2001 Mar.;75(3):588–93), Collins A K et al suggested a method of employing a coumarin fluorescent product as radiation dosimeter in radiation therapy (*Coumarin chemical dosimeter for radiation therapy*, Med Phys. 1994 Nov.;21(11): 1741–7), and Nairn R C et al described the usefulness of fluorescent probes in monitoring cell immunity (*Fluorescent probes for rapid tests of cellular immunoreactivity*, Pathology. 1984 Jan.;16(1):1–3).

The inventive fluorescent cannabinoids can also be used as a diagnostic tool to label and measure cells containing cannabinoid receptors. In human leukocytes, the CB2 receptors are found with particularly high abundance on B-cells, natural killer cells and macrophages. Leukocytes are the cells responsible for immunosurveillance and for the specificity of immune defense in humans. The quantification of the major types of human leukocytes has proved to be of great diagnostic and prognostic value in different pathologic conditions. As one example, count of peripheral blood natural killer cells is suggested as a useful index in prognosis of large cell lymphoma (Baumann M A et al, *Correlation of circulating natural killer cell count with prognosis in large cell lymphoma*, Cancer. 1986 Jun. 15;57(12):2309–12). Typically, quantification of lymphocytes employs immunofluorescent antibodies as lymphocyte markers. Therefore, a potential usefulness of this invention is that at least one inventive compound can be added to white blood cells to bind to the CB2 receptors therein. Fluorescent measurement techniques can be used to qualitatively and/or quantitatively assess the inventive compounds present and thereby label the cannabinoid receptors and provide information as to the quantity of receptors and white blood cells.

The inventive fluorescent cannabinoids can also be used as an imaging agent. Addition of at least one inventive compound to a tissue sample allows binding of the inventive compound to receptors therein. Subsequent excitation of the bound compound/tissue sample allows image analysis of the emitted light.

As used herein a "therapeutically effective amount" of a compound, is the quantity of a compound which, when administered to an individual or animal, results in a sufficiently high level of that compound in the individual or animal to cause a physiological response. The inventive compounds described herein, and physiologically acceptable salts thereof, have pharmacological properties when administered in therapeutically effective amounts for providing a physiological response useful to treat central and peripheral pain, neuropathy, neurodegenerative diseases including multiple sclerosis, Parkinson's disease, Huntington's chorea, Alzheimer's disease; mental disorders such as schizophrenia and depression; to prevent or reduce endotoxic shock and hypotensive shock; to modulate appetite; to modulate the immune system; to reduce fertility; to prevent or reduce diseases associated with motor function such as Tourette's syndrome; to prevent or reduce inflammation; to provide neuroprotection; to suppress memory; to produce peripheral vasodilation; to treat epilepsy, glaucoma, nausea associated with cancer chemotherapy as well as other ailments in which cannabinoid system is implicated.

The inventive compounds described herein, and physiologically acceptable salts thereof, have pharmacological properties when administered in therapeutically effective amounts for providing a physiological response useful to treat nausea associated with Aids wasting syndrome or to enhance appetite in AIDS wasting syndrome.

Typically, a "therapeutically effective amount" of an inventive compound is believed to range from about 5 mg/day to about 1,000 mg/day.

As used herein, an "individual" refers to a human. An "animal" refers to, for example, veterinary animals, such as dogs, cats, horses and the like, and farm animals, such as cows, pigs and the like.

The compound of the present invention can be administered by a variety of known methods, including, for example, orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

The following examples are given for purposes of illustration only in order that the present invention may be more fully understood. These examples are not intended to limit in any way the scope of the invention unless otherwise specifically indicated.

EXAMPLES

TABLE 1 illustrates some synthesized cannabinoids of the present invention (compounds 1–49). Compounds 1–27, 38 and 45–46 are representative fluorescent cannabinoids.

TABLE 1

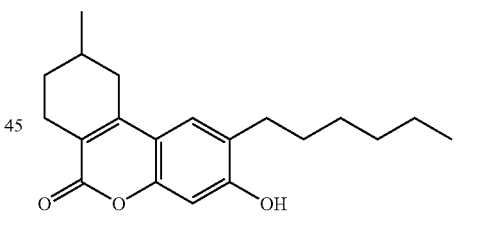

1

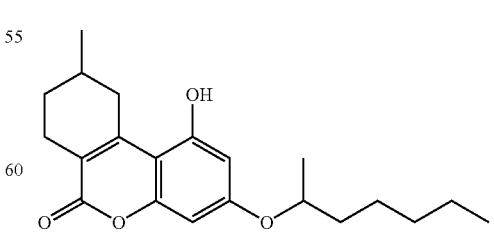

2

TABLE 1-continued
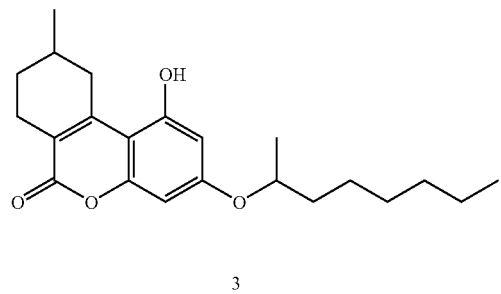
3
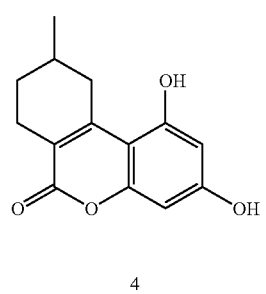
4
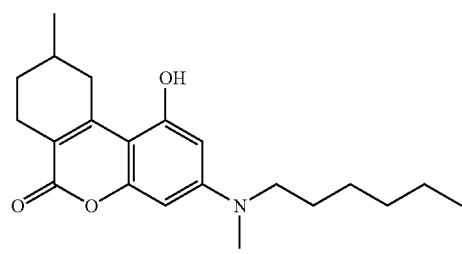
5
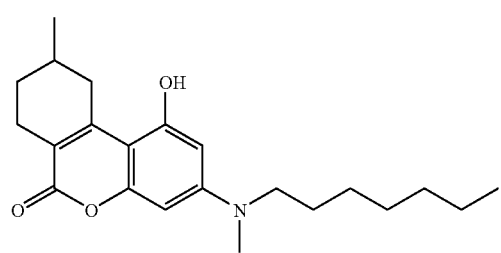
6
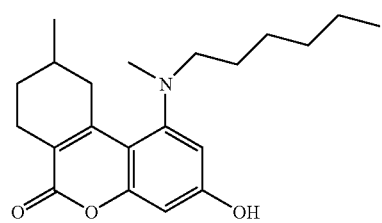
7
TABLE 1-continued
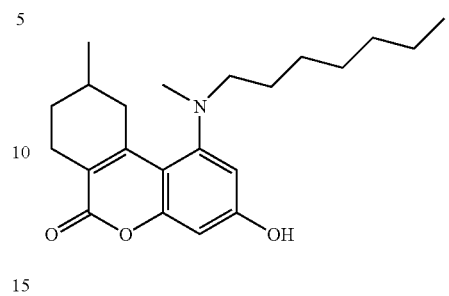
8
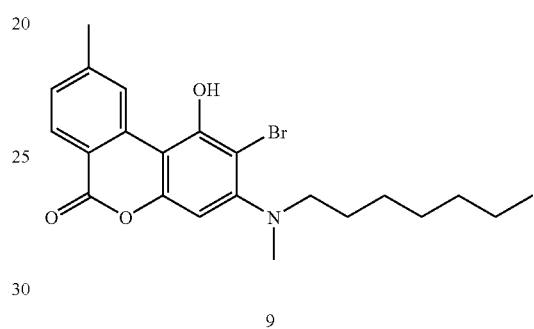
9
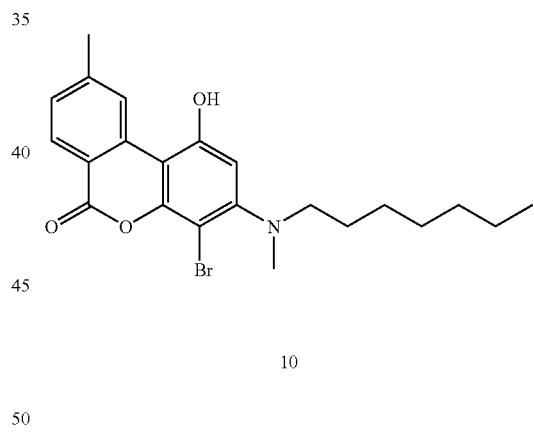
10
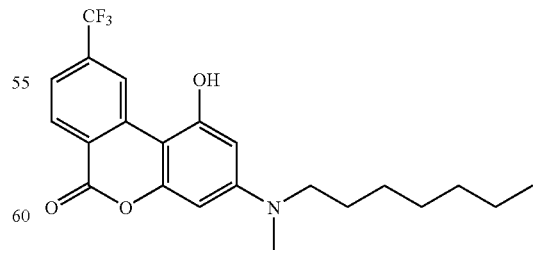
11

TABLE 1-continued
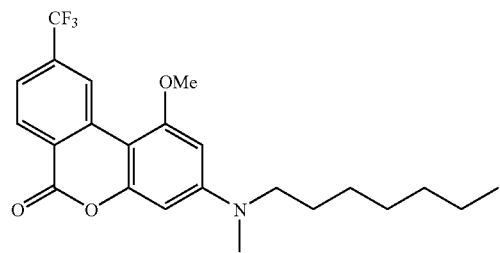
12
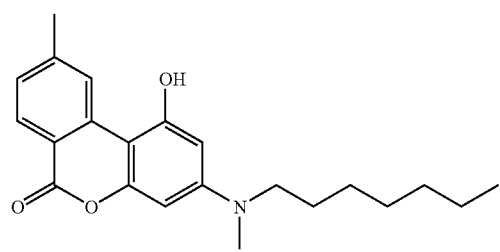
13
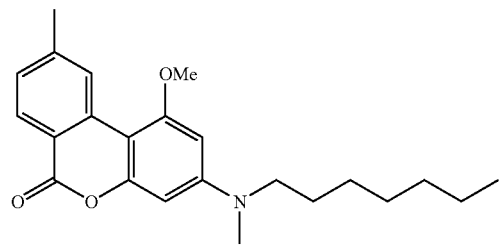
14
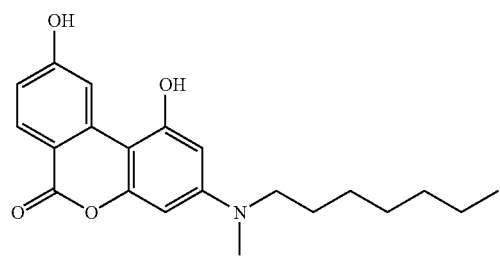
15
TABLE 1-continued
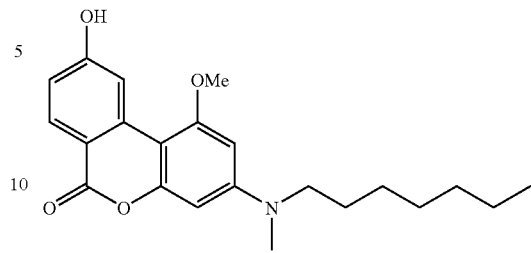
16
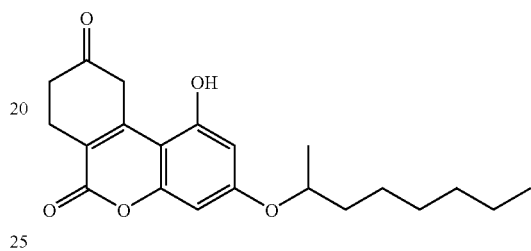
17
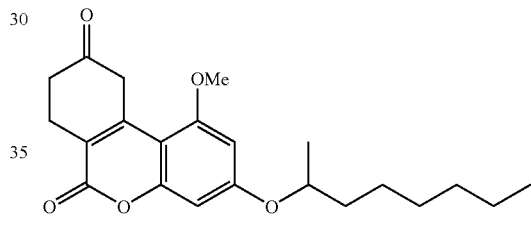
18
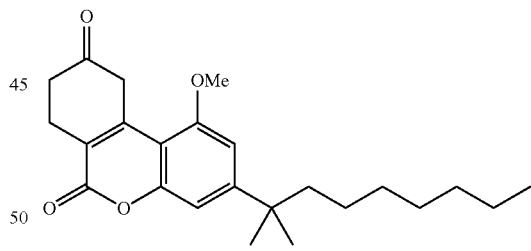
19
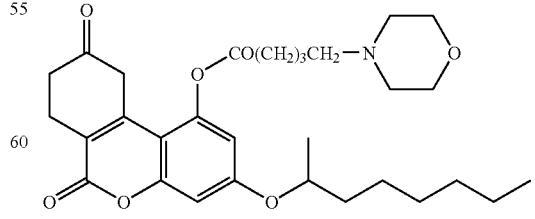
20

TABLE 1-continued
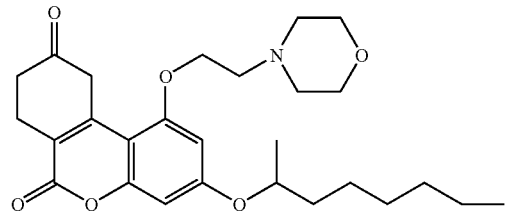
21
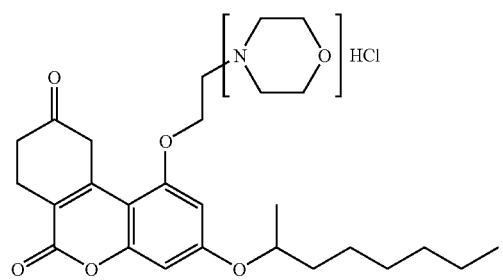
22
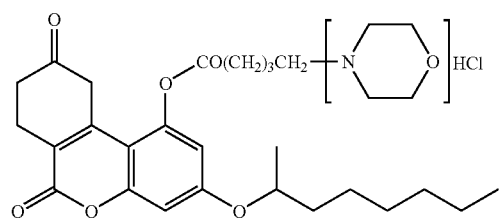
23
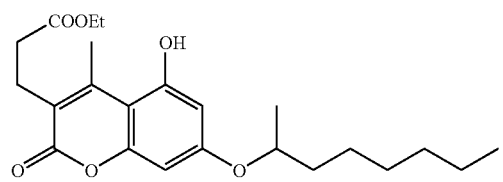
24
TABLE 1-continued
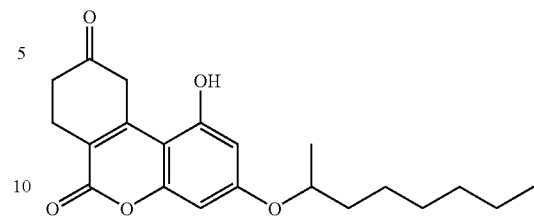
25
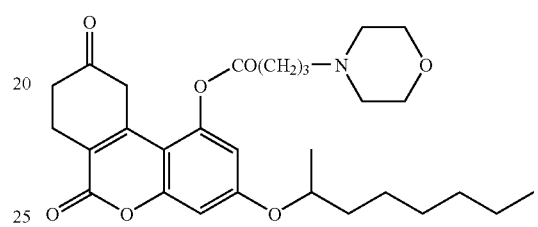
26
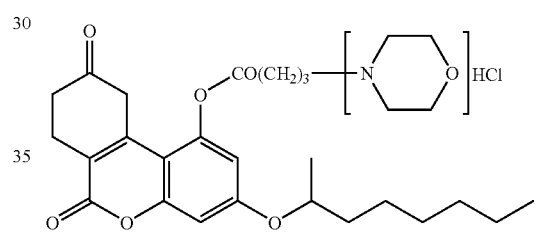
27
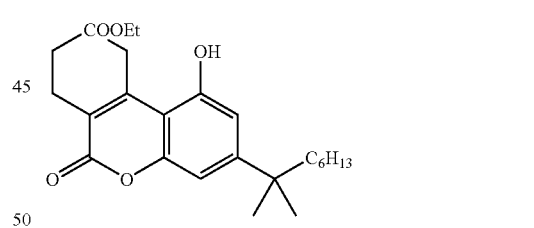
28
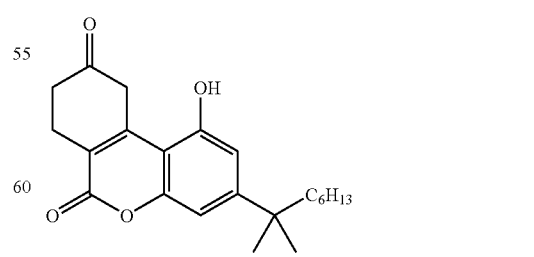
29

TABLE 1-continued
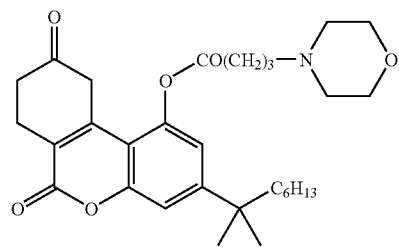
30
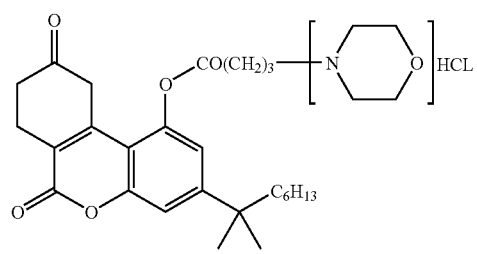
31
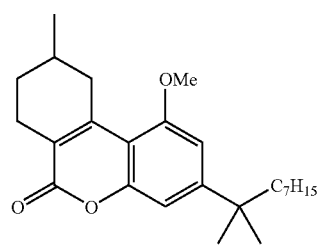
32
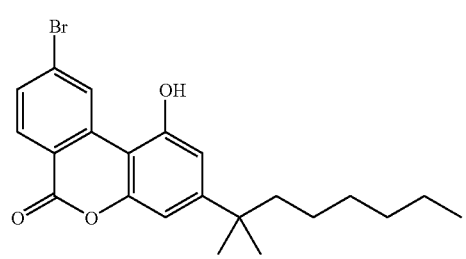
33
TABLE 1-continued
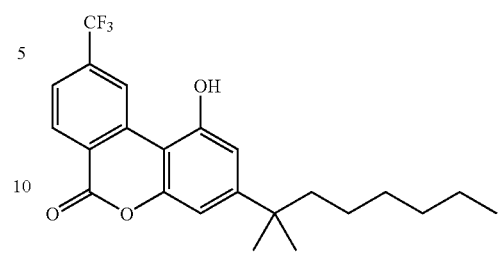
34
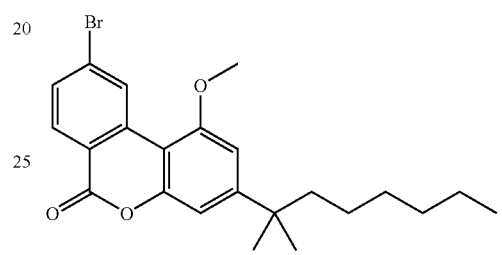
35
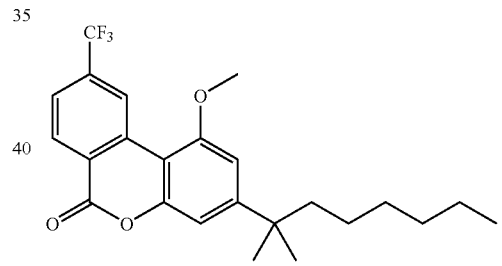
36
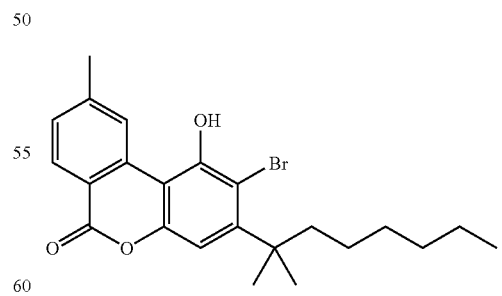
37

TABLE 1-continued
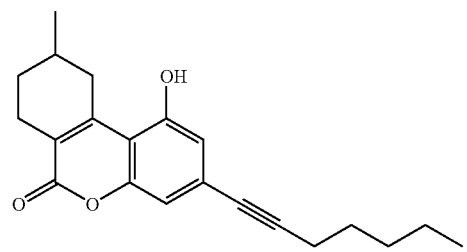
38
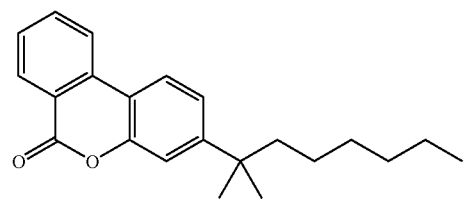
39
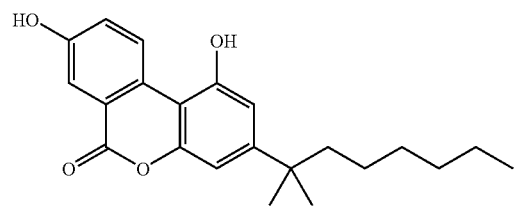
40
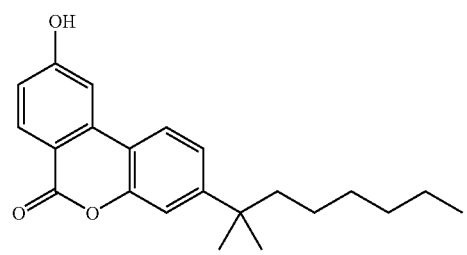
41
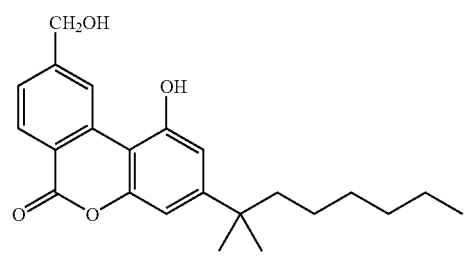
42
TABLE 1-continued
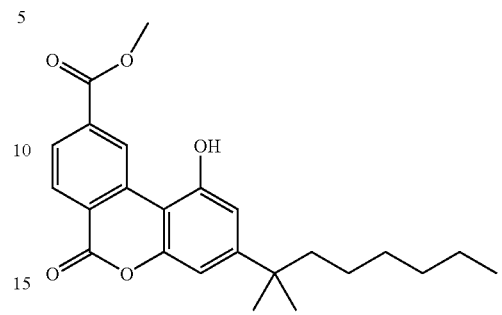
43
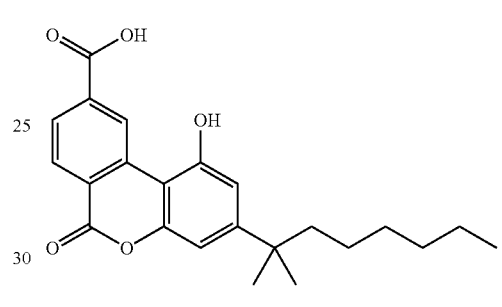
44
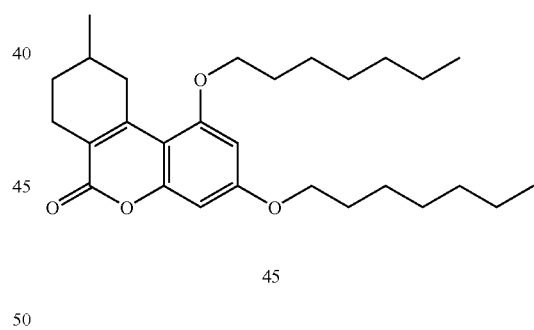
45
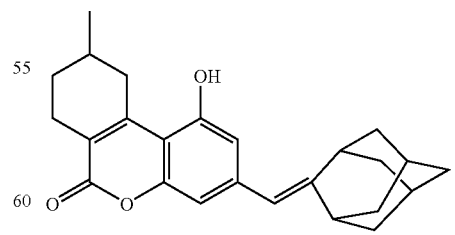
46

TABLE 1-continued

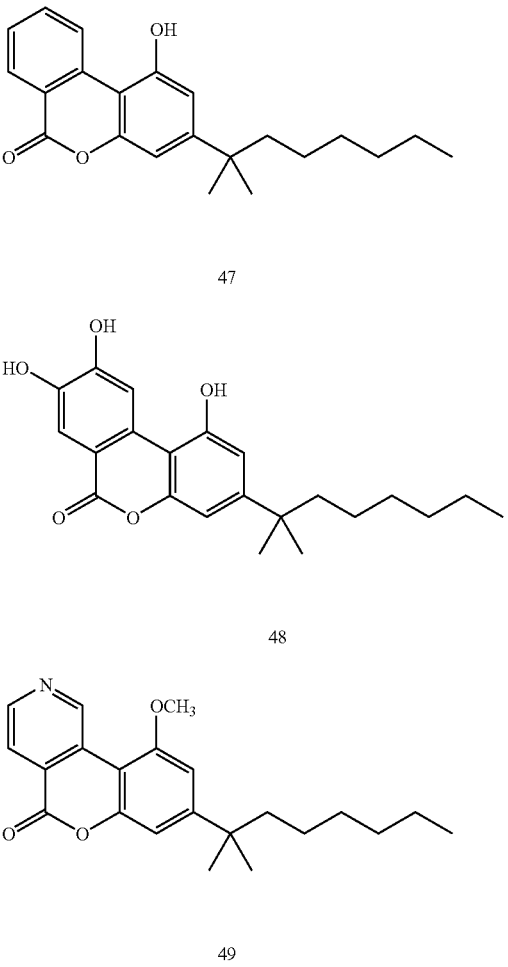

The fluorescent properties of some of the inventive compounds were examined using the following fluorescence assay protocol. All samples were processed in the same manner and diluted in J T BAKER PHOTREX Grade MeOH. Cuvettes and flasks were cleaned and rinsed with distilled water then rinsed twice with MeOH. Samples were kept in the freezer prior to testing. NSG Precision Quartz Cuvettes were used for absorption and spectral scans. Samples were diluted with methanol to a final volume of 5 mL. A 100× dilution of the samples in MeOH was performed. Absorption spectra were run using a Beckman DU-40 Spectrophotometer. Guided by absorption spectra, excitation and emission scans were run using an ISA Fluoromax-2 Fluorometer.

500 μL of MeOH was added into sample vial containing about 1 mg of testing compound, and aspirated with pipette to mix. 500 μL sample aliquot was then placed into 5 mL volumetric flask and brought up to volume with MeOH, and 5 mL was used as stock. Serial dilutions in 50 mL volumetric flasks were performed until final concentration of 100× reached. Dilution protocol was repeated for each sample. After dilution, 2.5 mL of sample was placed into a 3 mL Quartz cuvette and the cuvette was placed in ISA Fluoromax-2 Fluorometer. Absorption scan was run in Beckman DU-40 Spectrophotometer. Excitation and emission scans were run and spectral data were collected.

Some of the inventive fluorescent cannabinoid compounds exhibit strong fluorescence in the ultraviolet and visible wavelength ranges. Representative fluorescent data for some inventive compounds is shown in TABLE 2.

TABLE 2

| compound | Absorbance Peak (nm) | Mol Extinction 1/((Mol × cm)/L) | Fluorescence Excitation Peak (nm) | Fluorescence Emission Peak (nm) | Stoke's Shift (nm) |
|---|---|---|---|---|---|
| 1 | 327 | 1.50E+04 | 330 | 390 | 60 |
| 2 | 320 | 1.39E+04 | 326 | 423 | 97 |
| 5 | 364 | 1.86E+04 | 368 | 460 | 92 |
| 6 | 364 | 1.80E+04 | 367 | 460 | 93 |
| 8 | 405 | 1.14E+04 | 405 | 465 | 60 |
| 13 | 316 | 2.27E+04 | 319 | 519 | 200 |
| 16 | 317 | 2.18E+04 | 321 | 498 | 177 |
| 15 | 318 | 2.34E+04 | 320 | 502 | 182 |

Some of the inventive compounds were tested for CB2 receptor binding affinity and for CB1 receptor affinity (to determine selectivity for the CB2 receptor). As used herein, "binding affinity" is represented by the $K_i$ value which is the inhibition constant correlated with the concentration of an analog required to occupy the 50% of the total number (Bmax) of the receptors. The lower the $K_i$ value the higher the binding affinity. As used herein an analog is said to have "binding selectivity" if it has higher binding affinity for one receptor compared to the other receptor; e.g. a cannabinoid analog which has a $K_i$ of 0.1 nM for CB1 and 10 nM for CB2, is 100 times more selective for the CB1 receptor. For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107–118 (1981). The binding of the novel analogues to the CB1 cannabinoid receptor was assessed as described in W. A. Devane et al, *Determination and Characterization of a Cannabinoid Receptor in a Rat Brain*, Mol. Pharmacol., 34, 605–613 (1988) and A. Charalambous et al, 5'-*azido* $\Delta^8$-*THC: A Novel Photoaffinity Label for the Cannabinoid Receptor*, J. Med. Chem., 35, 3076–3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM $MgCl_2$ and 1 mM EDTA) at a pH 7.4. The suspension was incubated at 4° C. for 30 min. At the end of the incubation, the membranes were pelleted and washed three times with TME.

The treated membranes were subsequently used in the binding assay described below. Approximately 30 μg of membranes were incubated in silanized 96-well microtiter plate with TME containing 0.1% essentially fatty acid-free bovine serum albumin (BSA), 0.8 nM [$^3$H] CP-55,940, and various concentrations of test materials in a final volume of 200 μL. The assays were incubated for 1 hour at 30° C. and then immediately filtered using Packard Filtermate 196 harvester and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the assumptions of Cheng et al, *Relationship Between the Inhibition Constant ($K_i$) and the concentration of Inhibitor which causes 50% Inhibition ($IC_{50}$) of an Enzymatic Reaction*, Biochem. Pharmacol., 22, 3099–3102, (1973), which is incorporated by reference herein.

For the CB2 receptor binding studies, membranes were prepared from frozen mouse spleen essentially according to the procedure of P. R. Dodd et al, *A Rapid Method for Preparing Synaptosomes: Comparison with Alternative Procedures*, Brain Res., 226, 107–118 (1981) which is incorporated by reference herein. Silanized centrifuge tubes were used throughout to minimize receptor loss due to adsorption. The CB2 binding assay was conducted in the same manner as for the CB1 binding assay. The binding affinities ($K_i$) were also expressed in nanomoles (nM).

Some of the inventive compounds illustrated in TABLE 1 showed high affinities for the CB1 and CB2 cannabinoid receptors, with CB1 $K_i$ values as low as 6.0 nM and CB2 $K_i$ values as low as 0.6 nM. Some of the inventive compounds show CB2/CB1 selectivity of 760 in favor of the CB2 receptor.

TABLE 3

| Compound | CB1 (nM) | CB2 (nM) |
|---|---|---|
| 1 | 8610 | 5630 |
| 2 | 150 | 25 |
| 3 | 30 | 6 |
| 17 | 4185 | 1233 |
| 20 | 2003 | 1661 |
| 21 | 122 | 128 |
| 22 | 160 | 288 |
| 23 | 2577 | 824 |
| 5 | 50 | 3 |
| 6 | 9 | 0.7 |
| 7 | 6680 | 1685 |
| 8 | 6365 | 1479 |
| 13 | 140 | 16 |
| 9 | 1264 | 90 |
| 10 | 990 | 23 |
| 14 | 1305 | 148 |
| 15 | 304 | 0.4 |
| 16 | 8434 | 355 |
| 11 | 40 | 1 |
| 47 | 4787 | 6.6 |
| 48 | 1946 | 100.6 |
| 49 | 3758 | 35.4 |

Preparation of Compounds

General All the reagents and solvents used in the following reactions are available from Sigma-Aldrich Fine Chemicals of Milwaukee, Wis. and/or Lancaster Synthesis Inc. of Windham, N.H. at the highest available grade except where indicated. All reactions were carried out under scrupulously dry conditions unless otherwise stated. Work-up organic phases are dried over $Na_2SO_4$, and solvents are then removed under reduced pressure. Column chromatography was carried out by using active silica gel (230–400 mesh) available from Selecto Scientific of Suwanee, Ga. All compounds are demonstrated to be homogeneous by analytical TLC on pre-coated silica gel TLC plates (Whatman Ltd, Maidstone, Kent, England), and chromatograms are visualized by phosphomolybdic acid staining and UV lamp at wavelength of 254 nm. Structures are determined by $^1H$ NMR spectra recorded on Bruker DMX-500 MHz spectometers and Mass spectra obtained on a Hewlett Packard HP 6890 GC-MS instrument.

The inventive compounds were prepared generally using three types of reactions, von Pechmann Condensation, Oxazoline facilitated aromatic carbon-carbon coupling, and Suzuki Coupling Reaction. The preparation procedures include aspects of the following references, the disclosures of which are hereby incorporated by reference.

Alo, B. I.; Kandil, A.; Patil, P. A.; Sharp, M. J.; Siddiqui, M. A.; and Snieckus, V. *Sequential Directed Ortho Metalation-Boronic Acid Cross-Coupling Reactions. A general Regiospecific Route to Oxygenated Dibenzo[b,d]pyran-6-ones Related to Ellagic Acid*, J. Org. Chem. 1991, 56, 3763–3768. Beak, P.; and Brown, R A., *The Tertiary Amide as an Effective Director of Ortho Lithiation*, J. Org. Chem. 1982, 47, 34–36. Watanabe, T.; Miyaura, N.; Suzuki, A., *Synthesis of Sterically Hindered Biaryls via the Palladium Catalyzed Cross-Coupling Reaction of Arylboronic Acids or their Esters with Haloarenes*. Synlett 1992, 207–210. Morris, S,; Mechoulam, R.; and Irene, Y., *Halogenation of phenols and Phenyl ethers with Potassium Halides in the Presence of 18-Crown-6 on Oxidation with m-Chloroperbenzoic Acid*, J. Chem. Soc., Perkin Trans. 1 1987, 1423–1427. Rhee, M. H.; Vogel, Z.; Barg, J.; Bayewitch, M.; Levy, R.; Hanus, L.; Breuer, A.; and Mechoulam, R., *Cannabinol Derivatives: Binding to Cannabinoid Receptors and Inhibition of Adenylcyclase*, J. Med. Chem. 1997, 40, 3228–3233. Fahrenholtz, K. E., Lurie, M. and Kierstead, A R. W., *The Total Synthesis of dl-$\Delta^9$-Tetrahydrocannabinol and Four of Its Isomers*, J. Amer. Chem. Soc. 1967, 89:23, 5934-5941. Love, R. Bender, P. E., Dowalo, F., Macko, E., and Fowler, P., Cannabinoids. *Structure-Activity Studies Related to 1,2-Dimethylheptyl Derivatives*, J. Med. Chem 1973, 16, 1200–1206. Meyers, A., Reuman, M. *The Synthetic Utility of Oxazolines in Aromatic Substituion, Tetrahydron* 1985, 41, 837–860. Novak, J., Salemink, A., *Cannabis. Part 27.$^1$ Synthesis of 8-, 10-, and 11-Oxygenated Cannabinols*, J. Chem. Soc. Perkin Trans I. 1983, 2867–2871. Hattori, T., Suzuki, T., and Miyano, S., *A Practical and Efficient Method for the Construction of the Biphenyl Framework; Nucleophilic Aromatic Substitution on 2-Methoxybenzoates with Aryl Grignard Reagents*, J. Chem. Soc., Chem. Commun. 1991, 1375–1376.

Scheme 1

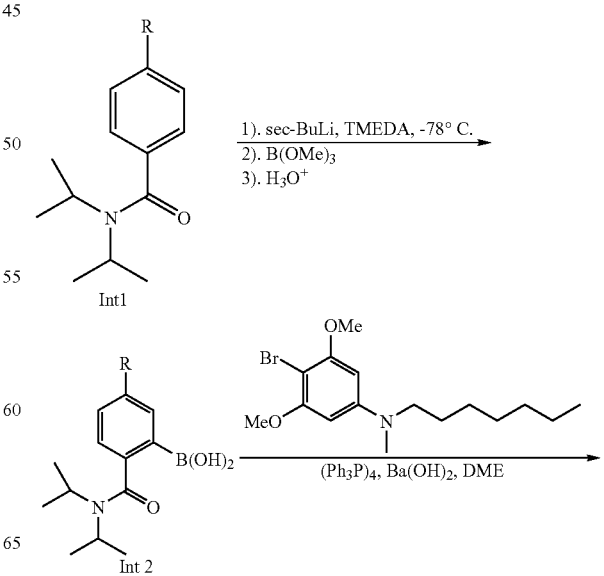

-continued
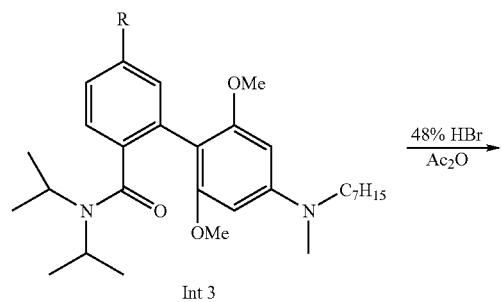
Int 3
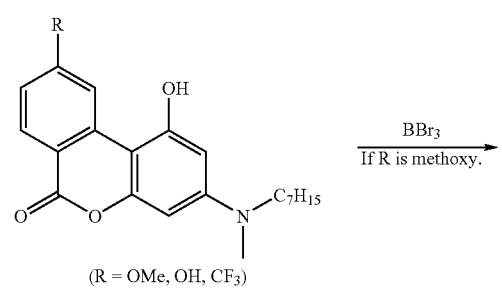
(R = OMe, OH, CF₃)
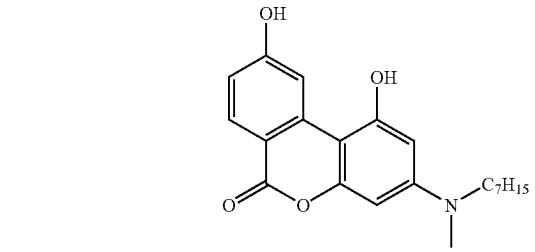
Scheme 2
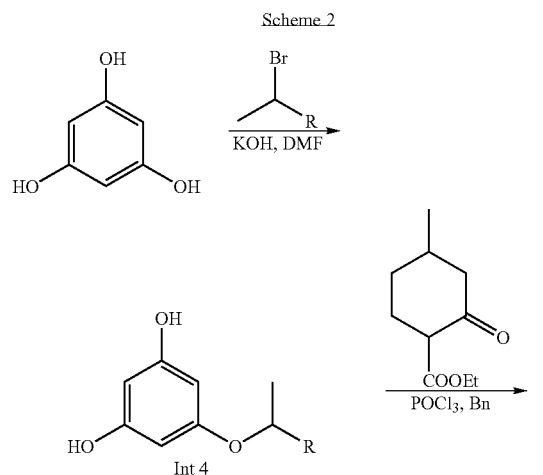
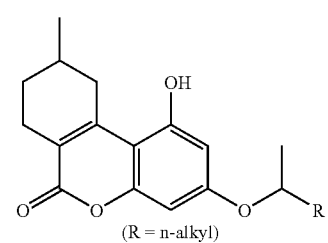
(R = n-alkyl)
Scheme 3
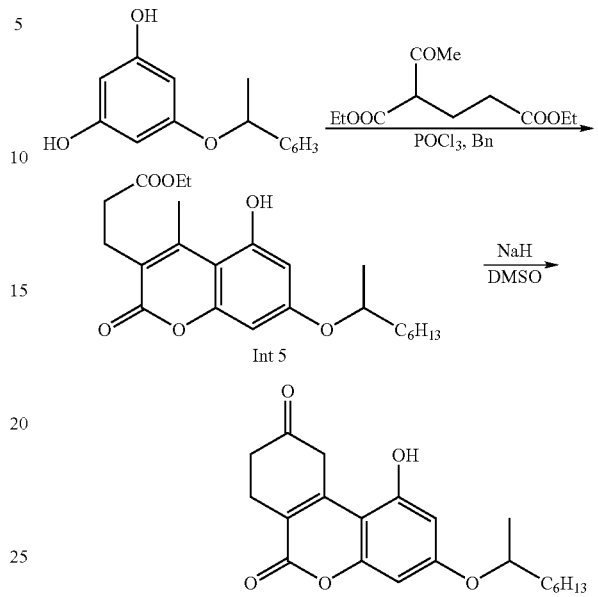
Int 5
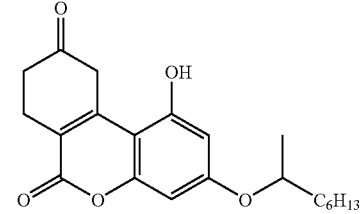
Scheme 4
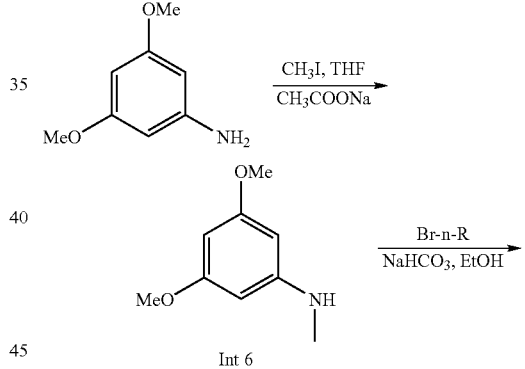
Int 6
Int 7
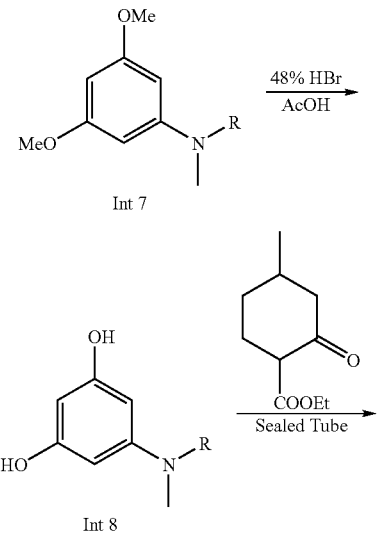
Int 8

-continued

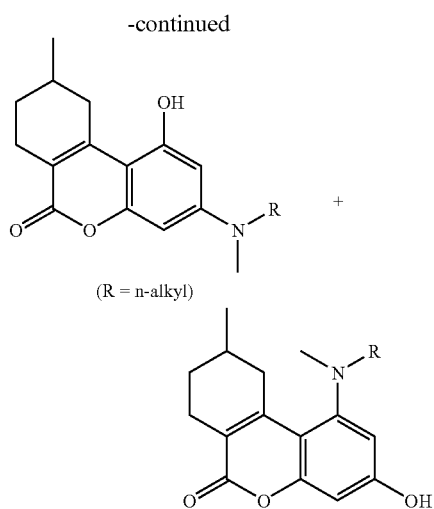

(R = n-alkyl)

General Procedure for Synthesis of Compounds Prepared by Scheme 1

2-(N,N-Diisopropylcarboxamido)-5-alkyl/alkoxyltrifloromethyl-phenylboronic acid (Int 2). Anhydrous tetrahydrofuran (250 ml) and TMEDA (9.05 ml, 60 mmol) was cooled to −78° C. under argon and, with stirring, 46.2 ml (60 mmol) of 1.3 M sec-butyllithium solution was added via syringe. The yellow solution was stirred at the same temperature for about 5 minutes and a solution of 5-substituted-N,N-diisopropylbenzamide Int 1 (50 mmol) in 50 ml of anhydrous THF was added dropwise. The reaction mixture was stirred at −78° C. for 1 hr and then 16.4 ml (150 mmol) of trimethylborate was added dropwise. The reaction mixture was allowed to warm to room temperature over night. The pH of the mixture was adjusted to about 6.5 by addition of 12% aqueous hydrochloric acid (about 50 ml) and concentrated by vacuum evaporation. The residue was extracted with dichloromethane. The combined organic extracts were dried over $Na_2SO_4$. Removal of solvent afforded a yellow or white form of solid product. The solid product was recrystallized in hot diethyl ether (general yield is about 95%).

N,N-Diisopropyl-5-methyl/methoxy/trifluoromethyl-1'6'dimethoxy-4'-(-(N-methyl,N-heptyl)-2-biphenylcarboxamide (Int 3). The above boronic acid (8 mmol), tetrakistriphenylphosphine palladium (0.5 mmol) and barium hydroxide octahydrate (10 mmol) and dimethoxyethane (20 ml) were mixed; 4 ml of water was added and the reaction mixture was stirred at room temperature under argon for 10 min. Then, a solution of 4 mmol of the (4-Bromo-3,5-dimethoxy-phenyl)-heptyl-methyl-amine* in 10 ml of dimethoxyethane was added with stirring and the reaction mixture was stirred and refluxed under argon for 24 hr. After cooling to room temperature, the catalyst was filtered out with the facilitation of celite and the filtrate was concentrated by vacuum evaporation. The residue was chromatographed on silica gel (25% ethyl acetate in petroleum ether) to provide the product in a general yield of 50%.

*Note: (4-Bromo-3,5-dimethoxy-phenyl)-heptyl-methyl-amine was prepared via bromination of Int 7: To a solution of Int 7 (800 mg, 3 mmol), tetraethylammonium chloride mono hydrate (TEACl, 20 mg)), 60 microliter anhydrous methanol in 15 ml of anhydrous dichloromethane, 0.16 ml of bromine was added dropwise at 0° C. The reaction was quenched by addition of 50 ml of 10% sodium bicarbonate aqueous solution after stirring at 0° C. under argon atmosphere for 1 hr. The organic layer was separated and washed quickly with water, brine, and dried over $Na_2SO_4$ under the protection of argon. Filtration and removal of solvent afforded the 0.97 g of the title compound, which was used directly in the reaction without further purification.

3-(N-methyl, N-heptyl)-1-hydroxy-9-methyl/methoxy/hydroxyltrifloromethyl-6H-dibenzo-[b,d]-pyran-6-one (13, 18, 19). 10 ml of 48% hydrobromic acid was added dropwise to the solution of 2 mmol of Int 3 in 10 ml of acetic anhydride at 0° C., then the reaction mixture was stirred and heated at 90° C. for 24 hr. To obtain the 5-hydroxy product, the reaction needs to carried out for 8 more hr and the addition of 10 ml of 48% hydrobromic acid after 24 hr. The reaction mixture was then cooled to room temperature and treated with 20% NaOH aqueous solution to pH about 8.5. The mixture was then extracted with ether. The ethereal solution was separated and washed with water, brine and dried over $Na_2SO_4$. Filtration and removal of solvent provided yellow solid crude product. The crude was chromatographed on silica gel (40% dichloromethane-petroleum ether) to afford the expected product in a general yield of 60%.

General Procedure for Synthesis of Compounds Prepared by Scheme 2

5-(1-Methylalkyloxy)resorcinol (Int 4). To a solution of phloroglucinol (100 mmol) and potassium hydroxide (34 mmol) in 40 ml of anhydrous DMF was added 2-bromo-n-alkane (105 mmol). After stirring and heating the mixture for 16 hr at 100° C., the reaction mixture was cooled to room temperature and then treated with 25 ml of acetic acid. The reaction mixture was then filtered, and the filtrate was extracted with ethyl ether following addition of 200 ml of water, the ethereal solution was separated and washed with water thoroughly. The ethereal solution was extracted with 15% sodium hydroxide aqueous solution. The alkaline solution was separated and washed with ether, acidified with 2N HCl, and extracted with ethyl ether. The ethereal extraction was separated and washed with water, brine, and dried with $Na_2SO_4$. Filtration and removal of solvent provided a crude brownish product. The crude product was chromatographed on silica gel (35% acetone-petroleum ether) to afford the expected product in a general yield of 30%.

1-Hydroxy-9-methyl-3-(1-methyl-alkyloxy)-7,8,9,10-tetrahydro-benzo[c]chromen-6-one (2 & 3). To a stirred solution of the resorcinol Int 4 (2 mmol) and 4-Methyl-2-oxo-cyclohexanecarboxylic acid ethyl ester (2.1 mmol) in 50 ml of anhydrous benzene was added $POCl_3$ (2.1 mmol) dropwise. After stirring for 2 hr at room temperature, the reaction mixture was refluxed for 20 min and allowed to stir at room temperature over night. The mixture was then treated with water and refluxed for 15 min, after which ethyl ether was added. The ethereal phase was then separated and washed with 10% $NaHCO_3$ aqueous solution, water, brine, and dried ($Na_2SO_4$). Filtration and removal of solvent provided yellow solid crude product. The crude product was chromatographed on silica gel (25% acetone-petroleum ether) to afford the expected product in a general yield of 70%.

General Procedure for Synthesis of Compounds Prepared by Scheme 3

3-[5-Hydroxy-4-methyl-7-(1-methyl-heptyloxy)-2-oxo-2H-chromen-3-yl]-propionic acid ethyl ester (Int 5). Phosphorous oxychloride (0.78 ml, 8.4 mmol) was added to a solution of 5-(1-Methylheptyloxy)resorcinol Int 4 (2.0 g, 8.4 mmol) and diethyl 2-acetylglutarate (2.0 g, 8.4 mmol) in 15 ml of anhydrous benzene. The reaction mixture was then refluxed at 90° C. for 4 hr under argon atmosphere. The mixture was then cooled to room temperature and treated with 25 ml of water. Ethyl ether was added. The ethereal extraction was separated and washed with water, 5% $NaHCO_3$, brine, and dried over $Na_2SO_4$. Filtration and removal of solvent provided 3.28 g of a yellow oily crude product. The crude product was chromatographed on silica gel (25% acetone-petroleum ether) to afford the expected product 0.78 g (22% yield). mp 116–117° C. The product was characterized by GS-MS, and 1D and 2D-$^1$H NMR.

1-Hydroxy-3-(1-methyl-heptyloxy)-7,10-dihydro-8H-benzo[c]chromere-6,9-dione (4). To a suspension of NaH (500 mg, 7.9 mmol, 60% dispersion in mineral oil, washed several times with n-hexane) in 4 ml of anhydrous DMSO, a solution of Int 5 (750 mg, 1.85 mmol) was added dropwise. The reaction mixture was stirred at room temperature over night. The reaction mixture was then poured onto ice containing 2 ml of 5% HCl. Ethyl ether was added to extract the solid crude product. The ethereal solution was separated and washed with water, brine, and dried over $Na_2SO_4$. Filtration and removal of solvent provided 640 mg yellow solid crude product. The crude product was chromatographed on silica gel (33% acetone-petroleum ether) to afford the expected product 340 mg (51% yield). mp 183–185° C. The product was characterized by GS-MS, and 1 D-$^1$H NMR.

General Procedure for Synthesis of Compounds Prepared by Scheme 4

(3,5-Dimethoxy-phenyl)-methyl-amine (Int 6). A solution of 3,5-dimethoxyaniline (13.8 g, 90 mmol), Iodomethane (12.7 g, 90 mmol), and sodium acetate (7.4 g, 90 mmol) in 100 ml of anhydrous THF was stirred under nitrogen atmosphere for 10 hr. Then, THF was removed by rotary evaporation. The crude product was partitioned between water and ethyl ether. The ethereal extraction was separated and washed with water, brine, and dried over $Na_2SO_4$. Filtration and removal of solvent provided 13.6 g of crude product. The crude product was chromatographed on silica gel (33% acetone-petroleum ether) to afford the expected product 4.5 g (27% yield).

(3,5-Dimethoxy-phenyl)-heptyl-methyl-amine (Int 7). A solution of Int 6 (5 g, 30 mmol), n-bromo-heptane (18.6 ml, 150 mmol), sodium hydrogen carbonate (3 g, 35 mmol) in 80 ml of anhydrous ethanol was stirred and heated at 90° C. for 16 hr. After cooling to room temperature, the solvent was removed by rotary evaporation. The crude product was partitioned between water and ethyl ether. The ethereal extraction was separated and washed with water, brine, and dried over $Na_2SO_4$. Filtration and removal of solvent provided 7.6 g of crude product. The crude product was chromatographed on silica gel (15% acetone-petroleum ether) to afford the expected product 4.8 g (64% yield). Another intermediate, Int 7 (3,5-dimethoxy-phenyl)-alkyl-methyl-amine), was prepared via the same procedure.

5-(Heptyl-methyl-amino)-resorcinol (Int 8). A mixture of Int 7 (570 mg, 2.3 mmol), 48% hydrobromic acid (13.5 ml) and glacial acetic acid (13.5 ml) was heated for 2 hr under argon atmosphere. The reaction mixture was then cooled to room temperature and treated with concentrated sodium hydroxide aqueous solution to pH 6.5. The resultant mixture was then extracted with ethyl ether. The ethereal extraction was separated and washed with water, brine, and dried over $Na_2SO_4$. Filtration and removal of solvent provided 550 mg of crude product. The crude product was chromatographed on silica gel (30% acetone-petroleum ether) to afford the expected product 500 mg (98% yield). Another intermediate, Int 8 (5-(alkyl-methyl-amino)-resorcinol), was prepared via the same procedure.

3-(Alkyl-methyl-amino)-1-hydroxy-9-methyl-7,8,9,10,-tetrahydro-benzo[c]chromen-6-one (9, 10, 11, 12). A solution of 2.0 mmol of 5-(N-methyl, N-alkyl amino)-resorcinol (Int 8) and 2.2 mmol of 4-Methyl-2-oxo-cyclohexanecarboxylic acid ethyl ester in 4 ml of anhydrous chloroform was stirred and heated at 110° C. under argon in a sealed tube for 16 hr. The reaction mixture was then cooled to room temperature. Solvent was removed by rotary evaporation. The resultant residue was chromatographed on silica gel (15% acetone-petroleum ether) to provide the two fluorescent products in a overall yield of 54%. The two isomers were characterized by GS-MS, and 1D and 2D-$^1$H NMR, the major product, 3-(alkyl-methyl-amino)-1-hydroxy-9-methyl-7,8,9,10,-tetrahydro-benzo[c]chromen-6-one (Int 9 or Int 10), was collected in a general yield of 35%.

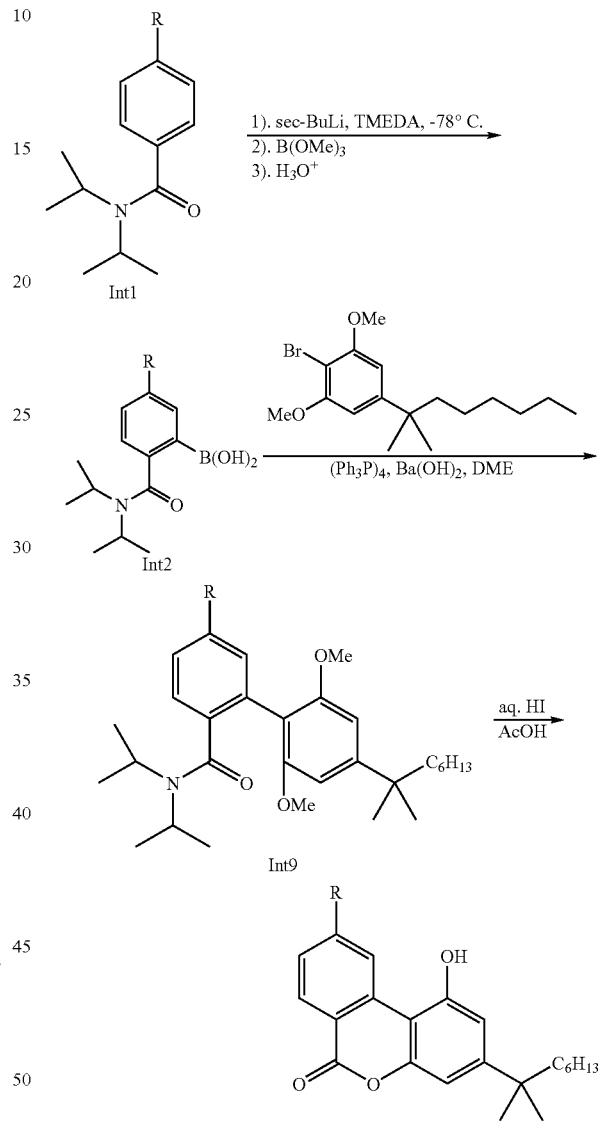

Scheme 5

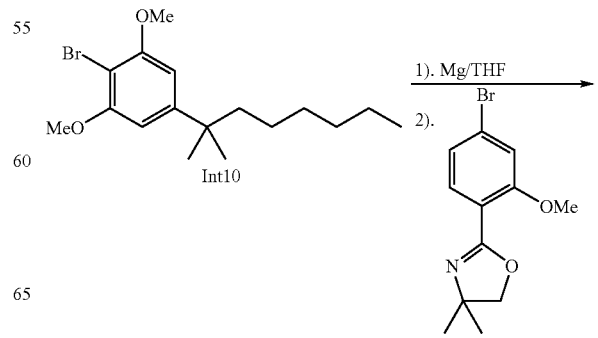

Scheme 6

-continued

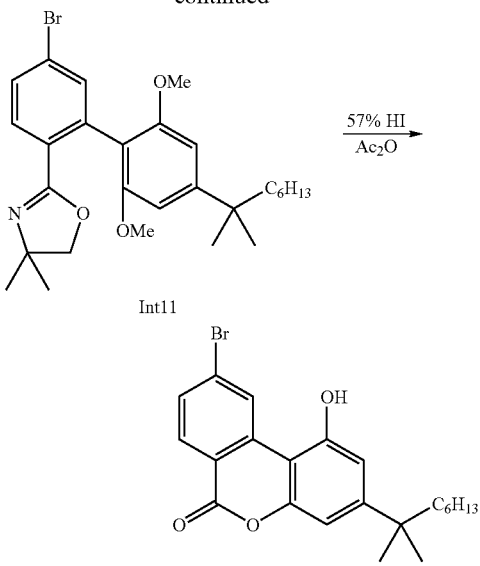

Int11

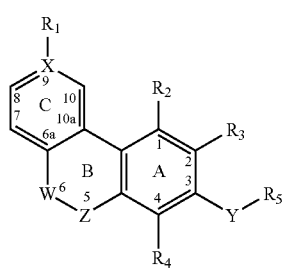

Synthesis of the compounds represented by Scheme 5 follows the similar method described in the procedures of Scheme 1. The synthesis of compounds represented by Scheme 6 was carried out by an oxazoline facilitated aromatic carbon-carbon coupling reaction as described by Meyers, A., Reuman, M in "*The Synthetic Utility of Oxazolines in Aromatic Substitution, Tetrahydron* 1985, 41, 837–860", and Novak, J., Salemink, A. in the "*Cannabis. Part 27.[1] Synthesis of 8-, 10-, and 11-Oxygenated Cannabinols, J. Chem. Soc. Perkin Trans I.* 1983, 2867–2871".

While preferred embodiments of the foregoing invention have been set forth for purposes of illustration, the foregoing description should not be deemed a limitation of the invention herein. Accordingly, various modifications, adaptations and alternatives may occur to one skilled in the art without departing from the spirit and scope of the present invention.

The invention claimed is:

1. A method of using a fluorescent cannabinoid compound as a fluorophore to generate a fluorescence emission signal comprising:

providing a cannabinoid compound having structural formula II below or a physiologically acceptable salt thereof,

II wherein:
W is C=O; Z is O; X is selected from C and CH; Y is selected from NH, N-alkyl, and N=N;
$R_1$ is any possible member selected from halogen, $N_3$, NCS, CN, $NO_2$, $NQ_1Q_2$, $OQ_3$, OAc, O-acyl, O-aroyl, NH-acyl, NH-aroyl, CHO, C(halogen)$_3$, COO$Q_3$, PO$_3$H$_2$, SO$_3$H, SO$_3$alkyl, SO$_2$NQ$_1$Q$_2$, CONQ$_1$Q$_2$, alkyl and alkyl substituted in any possible position with at least one substituent group, $Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members, $Q_3$ is selected from H, alkyl, alcohol and alkyl-NQ$_1$Q$_2$;

$R_2$ is selected from OH, OCH$_3$, OPO$_3$H$_2$, OSO$_3$H, OQ$_3$, O—COalkyl, O—COalkyl-T$_1$, O—CO-T$_1$, O-alkyl-T$_1$ and O-T$_1$, $T_1$ is in any possible position and is selected from PO$_3$H, SO$_3$H, an alkyl group containing from 1 to about 16 carbon atoms, tetrahydropyrrole, morpholine, thiomorpholine, piperazine, a heterocyclic ring and NQ$_1$Q$_2$, $T_1$ is optionally substituted in any possible position with at least one member selected from a substituent group, OPO$_3$H$_2$, OSO$_3$H, PO$_3$H$_2$, a heterocyclic ring and a heteroaromatic ring, $Q_3$ is selected from H, alkyl, alcohol and alkyl-NQ$_1$Q$_2$;

$R_3$ is selected from H, OH, halogen, C(halogen)$_3$, CN, N$_3$, NCS, NQ$_1$Q$_2$ and C1 to C4 alkyl, $Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members;

$R_4$ is selected from H, OH, halogen, C(halogen)$_3$, CN, N$_3$, NCS, NQ$_1$Q$_2$ and C1 to C4 alkyl;

$Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members; and $R_5$ is selected from -D$_1$-D$_2$-T$_2$ and -D$_2$-T$_2$ $D_1$, if present, is selected from alkyl, a carbocyclic ring, a heterocyclic ring, alkylamino and NH, $D_2$ is selected from an alkyl group having from one to about sixteen carbon atoms, a bicyclic ring, a tricyclic ring, a heterocyclic ring, an aromatic ring, a heteroaromatic ring, 1-adamantyl-T$_3$, 2-adamantyl-T$_3$, adamantan-1-ylmethyl-T$_3$, adamantan-2-ylidenemethyl-T$_3$, alkylamino, di-alkylamino and NH, $T_2$ is selected from, in any possible position, a substituent group and —CO-T$_4$, $T_3$ is an alkyl group having from 0 to about 9 carbon atoms, $T_4$ is selected from H, C(halogen)$_3$, OH, NH$_2$, NO$_2$, alkyl, alkoxy, a heterocyclic ring and a heteroaromatic ring;

exciting the cannabinoid compound with electromagnetic radiation; and detecting the electromagnetic radiation fluorescently emitted by the cannabinoid compound.

2. The method of claim 1, wherein the electromagnetic radiation fluorescently emitted by the compound is in the ultraviolet-visible wavelength ranges.

3. The method of claim 1, wherein the step of detecting comprises quantifying the electromagnetic radiation fluorescently emitted by the compound.

4. The method of claim 1 wherein $R_1$ is any possible member selected from halogen, OH, an alkyl group having 1 to about 5 carbon atoms and an alkyl group having 1 to about 5 carbon atoms and substituted in any possible position with at least one member selected from OH, CHO, COOH, C(halogen)$_3$, N$_3$, NCS, CN, PO$_3$H$_2$, SO$_3$H and SO$_3$alkyl.

5. The method of claim 1 wherein $R_5$ is selected from -D$_1$-D$_2$-T$_2$ and -D$_2$-T$_2$,
 D$_1$, if present, is selected from alkyl, a carbocyclic ring having 4 to 6 ring members and a heterocyclic ring having 4 to 6 ring members and $_{1,3}$ di-heteroatoms each heteroatom independently selected from O, S and N,
 D$_2$ is selected from an alkyl group having from one to about sixteen carbon atoms, a bicyclic ring, a tricyclic ring, 1-adamantyl-T$_3$, 2-adamantyl-T$_3$, adamantan-$_1$-ylmethyl-T$_3$, adamantan-2-ylidenemethyl-T$_3$, alkylamino, di-alkylamino and NH,
 T$_2$ is selected from, in any possible position, a substituent group and —CO-T$_4$,
  T$_3$ is an alkyl group having from 0 to about 9 carbon atoms, and
  T$_4$ is selected from alkyl, a heterocyclic ring and a heteroaromatic ring.

6. The method of claim 1 wherein:
X is C;
$R_1$ is selected from methyl, OH , CH$_2$OH, halogen and C(halogen)$_3$;
$R_2$ is selected from OH, OCH$_3$, OPO$_3$H$_2$, OSO$_3$H, OQ$_3$, O—COalkyl, O—COalkyl-T$_1$, O—CO-T$_1$, O-alkyl-T$_1$ and O-T$_1$,
 T$_1$ is in any possible position and is selected from PO$_3$H, SO$_3$H, an alkyl group containing from 1 to about 16 carbon atoms, tetrahydropyrrole, morpholine, thiomorpholine, piperazine, a heterocyclic ring and NQ$_1$Q$_2$,
 T$_1$ is optionally substituted in any possible position with at least one member selected from a substituent group, OPO$_3$H$_2$, OSO$_3$H, PO$_3$H$_2$, a heterocyclic ring and a heteroaromatic ring,
 Q$_3$ is selected from H, alkyl, alcohol and alkyl-NQ$_1$Q$_2$;
$R_3$ is selected from H, OH, halogen, C(halogen)$_3$, CN, N$_3$, NCS, NQ$_1$Q$_2$ and an alkyl group having 1 to about 4 carbon atoms,
 Q$_1$ and Q$_2$ are each independently selected from H and alkyl, or
 Q$_1$ and Q$_2$ together comprise part of a heterocyclic ring having about 4 to about 7 ring members and optionally one additional heteroatom selected from O, N and S, or
 Q$_1$ and Q$_2$ together comprise part of an imide ring having about 5 to about 6 members;
$R_4$ is selected from H, OH, halogen, C(halogen)$_3$, CN, N$_3$, NCS, NQ$_1$Q$_2$ and an alkyl group having 1 to about 4 carbon atoms,
 Q$_1$ and Q$_2$ are each independently selected from H and alkyl, or
 Q$_1$ and Q$_2$ together comprise part of a heterocyclic ring having about 4 to about 7 ring members and optionally one additional heteroatom selected from O, N and S, or
 Q$_1$ and Q$_2$ together comprise part of an imide ring having about 5 to about 6 members; and
$R_5$ is selected from -D$_1$-D$_2$-T$_2$ and -D$_2$-T$_2$,
 D$_1$, if present, is selected from a carbocyclic ring, a heterocyclic ring, alkylamino and NH,
 D$_2$ is selected from an alkyl group having from one to about sixteen carbon atoms, a bicyclic ring, a tricyclic ring, 1-adamantyl-T$_3$, 2-adamantyl-T$_3$, adamantan-1-ylmethyl-T$_3$, adamantan-2-ylidenemethyl-T$_3$, alkylamino, di-alkylamino and NH,
 T$_2$ is selected from, in any possible position, a substituent group and —CO-T$_4$,
  T$_3$ is an alkyl group having from 0 to about 9 carbon atoms,
  T$_4$ is selected from H, C(halogen)$_3$, OH, NH$_2$, NO$_2$, alkyl, alkoxy, alkylamino, di-alkylamino, a heterocyclic ring and a heteroaromatic ring.

7. The method of claim 1 wherein:
X is C;
$R_1$ is selected from methyl, OH and CH$_2$OH;
$R_2$ is selected from OH, OCH$_3$, OPO$_3$H$_2$, OSO$_3$H, OQ$_3$, O—COalkyl, O—COalkyl-T$_1$, O—CO-T$_1$, O-alkyl-T$_1$ and O-T$_1$,
 T$_1$ is in any possible position and is selected from PO$_3$H, SO$_3$H, an alkyl group containing from 1 to about 16 carbon atoms, tetrahydropyrrole, morpholine, thiomorpholine, piperazine, a heterocyclic ring and NQ$_1$Q$_2$,
 T$_1$ is optionally substituted in any possible position with at least one member selected from a substituent group, OPO$_3$H$_2$, OSO$_3$H, PO$_3$H$_2$, a heterocyclic ring and a heteroaromatic ring,
 Q$_3$ is selected from H, alkyl, alcohol and alkyl-NQ$_1$Q$_2$;
$R_3$ is selected from H, OH, halogen, C(halogen)$_3$, CN, N$_3$, NCS, NQ$_1$Q$_2$ and an alkyl group having 1 to about 4 carbon atoms,
 Q$_1$ and Q$_2$ are each independently selected from H and alkyl, or
 Q$_1$ and Q$_2$ together comprise part of a heterocyclic ring having about 4 to about 7 ring members and optionally one additional heteroatom selected from O, N and S, or
 Q$_1$ and Q$_2$ together comprise part of an imide ring having about 5 to about 6 members;
$R_4$ is selected from H, OH, halogen, C(halogen)$_3$, CN, N$_3$, NCS, NQ$_1$Q$_2$ and an alkyl group having $_1$ to about 4 carbon atoms,
 Q$_1$ and Q$_2$ are each independently selected from H and alkyl, or
 Q$_1$ and Q$_2$ together comprise part of a heterocyclic ring having about 4 to about 7 ring members and optionally one additional heteroatom selected from O, N and S, or
 Q$_1$ and Q$_2$ together comprise part of an imide ring having about 5 to about 6 members; and
$R_5$ is selected from -D$_1$-D$_2$-T$_2$ and -D$_2$-T$_2$,
D$_1$, if present, is selected from an alkyl, a carbocyclic ring having 4 to 6 ring members and a heterocyclic ring having 4 to 6 ring members and 1,3di-heteroatoms each heteroatom independently selected from O, S and N,
D$_2$ is selected from an alkyl group having from one to about sixteen carbon atoms, alkylamino, d-alkylamino, NH, a bicyclic ring, a tricyclic terpine, 1-adamantyl-T$_3$, 2-adamantyl-T$_3$, adamantan-1-ylmethyl-T$_3$ and adamantan-2-ylidenemethyl-T$_3$,
T$_2$ is selected from, in any possible position, a substituent group and —CO-T$_4$, $T_3$ is an alkyl group having from 0 to about 9 carbon atoms, and $T_4$ is selected from alkyl, C(halogen)$_3$ aminoalkyl, di-aminoalkyl, NH2, a heterocyclic ring and a heteroaromatic ring.

8. A test kit comprising a cannabimimetic compound having an endogenous fluorescent property and the structural formula

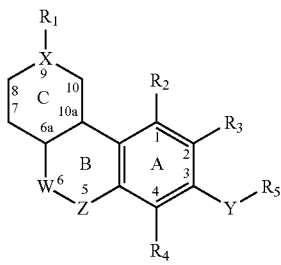

wherein:

Y is selected from NH, N-alkyl, and N=N

Z is O; X is selected from C and CH; and

W is C=O and the C ring is aromatic;

$R_1$ is any possible member selected from halogen, $N_3$, NCS, CN, $NO_2$, $NQ_1Q_2$, $OQ_3$, OAc, O-acyl, O-aroyl, NH-acyl, NH-aroyl, CHO, C(halogen)$_3$, $COOQ_3$, $PO_3H_2$, $SO_3H$, $SO_3$alkyl, $SO_2NQ_1Q_2$, $CONQ_1Q_2$, alkyl and alkyl substituted in any possible position with at least one substituent group, $Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members, $Q_3$ is selected from H, alkyl, alcohol and alkyl-$NQ_1Q_2$;

$R_2$ is selected from OH, $OCH_3$, $OPO_3H_2$, $OSO_3H$, $OQ_3$, O—COalkyl, O—COalkyl-$T_1$, O—CO-$T_1$, O-alkyl-$T_1$ and O-$T_1$, $T_1$ is in any possible position and is selected from $PO_3H$, $SO_3H$, an alkyl group containing from 1 to about 16 carbon atoms, tetrahydropyrrole, morpholine, thiomorpholine, piperazine, a heterocyclic ring and $NQ_1Q_2$, $T_1$ is optionally substituted in any possible position with at least one member selected from a substituent group, $OPO_3H_2$, $OSO_3H$, $PO_3H_2$, a heterocyclic ring and a heteroaromatic ring, $Q_3$ is selected from H, alkyl, alcohol and alkyl-$NQ_1Q_2$;

$R_3$ is selected from H, OH, halogen, C(halogen)$_3$, CN, $N_3$, NCS, $NQ_1Q_2$ and C1 to C4 alkyl, $Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members;

$R_4$ is selected from H, OH, halogen, C(halogen)$_3$, CN, $N_3$, NCS, $NQ_1Q_2$ and C1 to C4 alkyl;

$Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members; and $R_5$ is selected from -$D_1$-$D_2$-$T_2$ and -$D_2$-$T_2$, $D_1$, if present, is selected from alkyl, a carbocyclic ring, a heterocyclic ring, alkylamino and NH, $D_2$ is selected from an alkyl group having from one to about sixteen carbon atoms, a bicyclic ring, a tricyclic ring, a heterocyclic ring, an aromatic ring, a heteroaromatic ring, 1-adamantyl-$T_3$, 2-adamantyl-$T_3$, adamantan-1-ylmethyl-$T_3$, adamantan-2-ylidenemethyl-$T_3$, alkylamino, di-alkylamino and NH, $T_2$ is selected from, in any possible position, a substituent group and —CO-$T_4$, $T_3$ is an alkyl group having from 0 to about 9 carbon atoms, $T_4$ is selected from H, C(halogen)$_3$, OH, $NH_2$, $NO_2$, alkyl, alkoxy, a heterocyclic ring and a heteroaromatic ring.

9. A compound of formula II, and physiologically acceptable salts thereof,

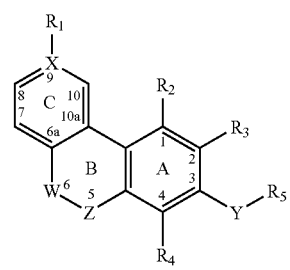

wherein:

W is C=O;

X is selected from C and CH;

Y is selected from NH, N-alkyl and N=N;

Z is O;

$R_1$ is any possible member selected from halogen, $N_3$, NCS, CN, $NO_2$, $NQ_1Q_2$, $OQ_3$, OAc, O-acyl, O-aroyl, NH-acyl, NH-aroyl, CHO, C(halogen)$_3$, $COOQ_3$, PO3$H_2$, $SO_3H$, $SO_3$alkyl, $SO_2NQ_1Q_2$, $CONQ_1Q_2$, alkyl and alkyl substituted in any possible position with at least one substituent group, $Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members, $Q_3$ is selected from H, alkyl, alcohol and alkyl-$NQ_1Q_2$;

$R_2$ is selected from H OH, $OCH_3$, $OPO_3H_2$, $OSO_3H$, $OQ_3$, O—COalkyl, O—COalkyl-$T_1$, O—CO-$T_1$, O-alkyl-$T_1$ and O-$T_1$, $T_1$ is in any possible position and is selected from $PO_3H$, $SO_3H$, an alkyl group containing from 1 to about 16 carbon atoms, tetrahydropyrrole, morpholine, thiomorpholine, piperazine, a heterocyclic ring and $NQ_1Q_2$, $T_1$ is optionally substituted in any possible position with at least one member selected from a substituent group, $OPO_3H_2$, $OSO_3H$, $PO_3H_2$, a heterocyclic ring and a heteroaromatic ring, $Q_3$ is selected from H, alkyl, alcohol and alkyl-$NQ_1Q_2$;

$R_3$ is selected from H, OH, halogen, C(halogen)$_3$, CN, $N_3$, NCS, $NQ_1Q_2$ and C1 to C4 alkyl, $Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members;

$R_4$ is selected from H, OH, halogen, C(halogen)$_3$, CN, $N_3$, NCS, $NQ_1Q_2$ and C1 to C4 alkyl;

$Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members; and $R_5$ is selected from -$D_1$-$D_2$-$T_2$ and -$D_2$-$T_2$, $D_1$, if present, is selected from alkyl, a carbocyclic ring, a heterocyclic ring, alkylamino and NH, $D_2$ is selected from an alkyl group having from one to about sixteen carbon atoms, a bicyclic ring, a tricyclic ring, a heterocyclic ring, an aromatic ring, a heteroaromatic ring, 1-adamantyl-$T_3$, 2-adamantyl-$T_3$, adamantan-1-ylmethyl-$T_3$, adamantan-2-ylidenemethyl-$T_3$, alkylamino, di-alkylamino and NH, $T_2$ is selected from, in any possible position, a substituent group and —CO-$T_4$, $T_3$ is an alkyl group having from 0 to about 9 carbon atoms, $T_4$ is selected from H, C(halogen)$_3$, OH, $NH_2$, $NO_2$, alkyl, alkoxy, a heterocyclic ring and a heteroaromatic ring.

10. The compound of claim 3 wherein $R_1$ is any possible member selected from halogen, C(halogen)$_3$, alkyl amino, di-alkylamino, $NH_2$, OH, an alkyl group having 1 to about 5 carbon atoms and an alkyl group having 1 to about 5 carbon atoms and substituted in any possible position with at least one member selected from OH, CHO, COOH, C(halogen)$_3$, $N_3$, NCS, CN, $PO_3H_2$, $SO_3H$ and $SO_3$alkyl.

11. The compound of claim 9 wherein $R_5$ is selected from -$D_1$-$D_2$-$T_2$ and -$D_2$-$T_2$, $D_1$, if present, is selected from alkyl, a carbocyclic ring having 4 to 6 ring members and a heterocyclic ring having 4 to 6 ring members and 1,3di-heteroatoms each heteroatom independently selected from O, S and N, $D_2$ is selected from an alkyl group having from one to about sixteen carbon atoms, a bicyclic ring, a tricyclic terpine, 1-adamantyl-$T_3$, 2-adamantyl-$T_3$, adamantan-1-ylmethyl-$T_3$, adamantan-2-ylidenemethyl-$T_3$, alkylamino, di-alkylamino and NH $T_2$ is selected from, in any possible position, a substituent group and —CO-$T_4$, $T_3$ is an alkyl group having from 0 to about 9 carbon atoms, and $T_4$ is selected from alkyl, a heterocyclic ring and a heteroaromatic ring.

12. The compound of claim 9 wherein:

X is C;

$R_1$ is selected from methyl, OH, $CH_2OH$, halogen and C(halogen)$_3$;

$R_2$ is selected from OH, $OCH_3$, $OPO_3H_2$, $OSO_3H$, $OQ_3$, O—COalkyl, O—COalkyl-$T_1$, O—CO-$T_1$, O-alkyl-$T_1$ and O-$T_1$, $T_1$ is in any possible position and is selected from $PO_3H$, $SO_3H$, an alkyl group containing from 1 to about 16 carbon atoms, tetrahydropyrrole, morpholine, thiomorpholine, piperazine, a heterocyclic ring and $NQ_1Q_2$, $T_1$ is optionally substituted in any possible position with at least one member selected from a substituent group, $OPO_3H_2$, $OSO_3H$, $PO_3H_2$, a heterocyclic ring and a heteroaromatic ring, $Q_3$ is selected from H, alkyl, alcohol and alkyl-$NQ_1Q_2$;

$R_3$ is selected from H, OH, halogen, C(halogen)$_3$, CN, $N_3$, NCS, $NQ_1Q_2$ and an alkyl group having $_1$ to about 4 carbon atoms, $Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members;

$R_4$ is selected from H, OH, halogen, C(halogen)$_3$, CN, $N_3$, NCS, $NQ_1Q_2$ and an alkyl group having 1 to about 4 carbon atoms, $Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members; and $R_5$ is selected from -$D_1$-$D_2$-$T_2$ and -$D_2$-$T_2$, $D_1$, if present, is selected from alkyl, a carbocyclic ring, a heterocyclic ring, alkylamino and NH, $D_2$ is selected from an alkyl group having from one to about sixteen carbon atoms, a bicyclic ring, a tricyclic ring, 1-adamantyl-$T_3$, 2-adamantyl-$T_3$, adamantan-1-ylmethyl-$T_3$, adamantan-2-ylidenemethyl-$T_3$, alkylamino, di-alkylamino and NH, $T_2$ is selected from, in any possible position, a substituent group and —CO-$T_4$, $T_3$ is an alkyl group having from 0 to about 9 carbon atoms, $T_4$ is selected from H, C(halogen)$_3$, OH, $NH_2$, $NO_2$, alkyl, alkoxy, alkylamino, di-alkylamino, a heterocyclic ring and a heteroaromatic ring.

13. The compound of claim 9 wherein:

X is C;

$R_1$ is selected from methyl, OH and $CH_2OH$;

$R_2$ is selected from OH, $OCH_3$, $OPO_3H_2$, $OSO_3H$, $OQ_3$, O—COalkyl, O—COalkyl-$T_1$, O—CO-$T_1$, O-alkyl-$T_1$ and O-$T_1$, $T_1$ is in any possible position and is selected from $PO_3H$, $SO_3H$, an alkyl group containing from 1 to about 16 carbon atoms, tetrahydropyrrole, morpholine, thiomorpholine, piperazine, a heterocyclic ring and $NQ_1Q_2$, $T_1$ is optionally substituted in any possible position with at least one member selected from a substituent group, $OPO_3H_2$, $OSO_3H$, $PO_3H_2$, a heterocyclic ring and a heteroaromatic ring, $Q_3$ is selected from H, alkyl, alcohol and alkyl-$NQ_1Q_2$;

$R_3$ is selected from H, OH, halogen, C(halogen)$_3$, CN, $N_3$, NCS, $NQ_1Q_2$ and an alkyl group having 1 to about 4 carbon atoms, $Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members;

R4 is selected from H, OH, halogen, C(halogen)$_3$, CN, $N_3$, NCS, $NQ_1Q_2$ and an alkyl group having 1 to about 4 carbon atoms, $Q_1$ and $Q_2$ are each independently selected from H and alkyl, or $Q_1$ and $Q_2$ together comprise part of a heterocyclic ring having about 4 to about 7 ring members and optionally one additional heteroatom selected from O, N and S, or $Q_1$ and $Q_2$ together comprise part of an imide ring having about 5 to about 6 members; and $R_5$ is selected from -$D_1$-$D_2$-$T_2$ and -$D_2$-$T_2$, $D_1$, if present, is selected from alkyl, a carbocyclic ring having 4 to 6 ring members and a heterocyclic ring having 4 to 6 ring members and 1,3di-heteroatoms each heteroatom independently selected from O, S and N, $D_2$ is selected from an alkyl group having from one to about sixteen carbon atoms, alkylamino, di-alkylamino, NH, a bicyclic ring, a tricyclic ring, 1-adamantyl-$T_3$, 2-adamantyl-$T_3$, adamantan-1-ylmethyl-$T_3$ and adamantan-2-ylidenemethyl-$T_3$, $T_2$ is selected from, in any possible position, a substituent group and —CO-$T_4$, $T_3$ is an alkyl group having from 0 to about 9 carbon atoms, and $T_4$ is selected from alkyl, C(halogen)$_3$ aminoalkyl, di-aminoalkyl, $NH_2$, a heterocyclic ring and a heteroaromatic ring.

14. A pharmaceutical composition comprising a therapeutically effective amount of at least one compound of claim 9 or a physiologically acceptable salt thereof.

15. A method of modulating at least one of the CB1 and CB2 cannabinoid receptors in an individual or animal comprising administering to the individual or animal a therapeutically effective amount of at least one compound of claim 9 or a physiologically acceptable salt thereof.

* * * * *

UNITED STATES PATENT AND TRADEMARK OFFICE
CERTIFICATE OF CORRECTION

PATENT NO. : 7,183,313 B2
APPLICATION NO. : 10/647544
DATED : February 27, 2007
INVENTOR(S) : Makriyannis et al.

It is certified that error appears in the above-identified patent and that said Letters Patent is hereby corrected as shown below:

On the Title Page, Item -75- Inventors: delete "Xin-Zhong Lai, Storrs, CT (US)".

Column 40:

Line 47, after "-$D_2$-$T_2$" insert --,--.

Column 41:

Line 22, delete "adamantan-$_1$-" and substitute -- adamantan-1- --.

Column 42:

Line 46, after "having" delete "$_1$" and substitute --1--.

Column 44:

Line 50, delete "PO3$H_2$" and substitute --$PO_3H_2$--.

Line 63, delete "H OH," and substitute --OH,--.

Column 45:

Line 46, delete "claim 3" and substitute --claim 9--.

UNITED STATES PATENT AND TRADEMARK OFFICE
CERTIFICATE OF CORRECTION

PATENT NO. : 7,183,313 B2
APPLICATION NO. : 10/647544
DATED : February 27, 2007
INVENTOR(S) : Makriyannis et al.

It is certified that error appears in the above-identified patent and that said Letters Patent is hereby corrected as shown below:

Column 46:

Line 21, delete "having $_1$ to about 4" and substitute --having 1 to about 4--.

Signed and Sealed this

Fifteenth Day of May, 2007

JON W. DUDAS
*Director of the United States Patent and Trademark Office*